United States Patent
FitzGerald et al.

(10) Patent No.: US 6,881,718 B1
(45) Date of Patent: Apr. 19, 2005

(54) DISULFIDE CONJUGATED CELL TOXINS AND METHODS OF MAKING AND USING THEM

(75) Inventors: David J. FitzGerald, Rockville, MD (US); Michael J. Iadarola, Washington, DC (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 481 days.

(21) Appl. No.: 10/110,934

(22) PCT Filed: Oct. 20, 2000

(86) PCT No.: PCT/US00/29064

§ 371 (c)(1),
(2), (4) Date: Apr. 17, 2002

(87) PCT Pub. No.: WO01/31020

PCT Pub. Date: May 3, 2001

Related U.S. Application Data

(60) Provisional application No. 60/161,159, filed on Oct. 22, 1999.

(51) Int. Cl.$^7$ .............................. C07K 1/36; C07K 2/00; A61K 38/00
(52) U.S. Cl. .............................. 514/2; 514/14; 514/15; 530/300; 530/344
(58) Field of Search .............................. 514/2, 14, 15; 530/300, 344

(56) References Cited

U.S. PATENT DOCUMENTS

| | | | | |
|---|---|---|---|---|
| 5,141,248 A | * | 8/1992 | Haldric et al. .............. | 280/777 |
| 5,169,933 A | * | 12/1992 | Anderson et al. ......... | 530/391.3 |
| 5,633,351 A | * | 5/1997 | Reed ....................... | 530/391.1 |
| 5,663,250 A | * | 9/1997 | Potter et al. ............... | 526/178 |
| 5,667,255 A | * | 9/1997 | Kato ......................... | 285/133.4 |
| 5,668,255 A | * | 9/1997 | Murphy ..................... | 530/350 |
| 5,747,641 A | | 5/1998 | Frankel et al. | |
| 6,632,440 B1 | * | 10/2003 | Quinn et al. ............. | 424/239.1 |

FOREIGN PATENT DOCUMENTS

WO    WO97/13410 A1    4/1997

OTHER PUBLICATIONS

D H Hoch, et al. Channels Formed by Botulinum, Tetanus, and Diphtheria Toxins in Planar Lipid Bilayers: Relevance to Translocation of Proteins across Membranes. Proc. Natl. Acad. Sci. USA (1985) 82, 1692–1696.*

Benoliel, Rafael, et al., "Actions of intrathecal diphtheria toxin–substance P fusion protein on models of persistent pain," *Pain* (1999) 79: 243–253.

Bergstrom, Lena et al., "Sulfhydryl reagents have different effects on substance P and Neurokinin B binding sites on cortical synaptosomes in the Rat," *Neuropeptides* (1987) 9: 151–159.

(Continued)

*Primary Examiner*—Bruce R. Campell
*Assistant Examiner*—Andrew D. Kosar
(74) *Attorney, Agent, or Firm*—Townsend and Townsend and Crew LLP

(57) ABSTRACT

The invention pertains to the discovery of novel disulfide linked cell toxins which can ablate NK-1 receptor expressing cells. These toxins are used as pharmaceutical compositions for the ablation of NK1 receptor expressing cells and comprise a substance P (SP)-*Pseudomonas* exotoxin disulfide linked conjugate. The invention also includes methods of making and using these toxins and pharmaceutical compositions.

19 Claims, 4 Drawing Sheets

OTHER PUBLICATIONS

Buechler, Ying Ji, et al., "Synthesis and characterization of a homogeneouse chemical conjugate between basic fibroblast growth factor and saporin," *Eur. J. Biochem.* (1995) 234: 706–713.

Faulstich, Heinz, et al., "Interchain and intrachain crosslinking of actin thiols by a bifunctional thiol reagent," *FEBS Letters* (1992) 302(3): 201–205.

Fisher, Caroline E., et al., "*Genetic construction and properties of a diphtheria toxin–related substance P fusion protein: In vitro destruction of cells bearing substance P receptors,*" *Proc. Natl. Acad. Sci. USA* (1996) 93: 7341–7345.

FitzGerald, David J., "Construction of Immunotoxins Using *Pseudomonas* Exotoxin A," *Methods in Enzymology* (1987) 151: 139–145.

FitzGerald, D.J., "How can we target cytotoxins to destroy subclasses of nociceptors?, " *Towards a New Pharmacotherapy of Pain* (1991) John Wiley & Sons Ltd., pp. 69–81.

Goettl, Virginia M., et al., "An antagonist of substance P N–terminal fragments, D–substance P(1–7), reveals that both nociceptive and antinociceptive effects are induced by substance P N–terminal activity during noxious chemical stimulation," *Brain Research* (1998) 780: 80–85.

Iadarola, Michael J., et al., "Good Pain, Bad Pain," *Science* (1997) 278: 239–240.

Mansfield, Elizabeth, et al., "Characterization of RFB4–*Pseudomonas* exotoxin A immunotoxins targeted to CD22 on B–cell malignancies," *Bioconjugate Chem.* (1996) &: 557–563.

Mantyh, Patrick W., et al., "Inhibition of hyperalgesia by ablation of lamina 1 spinal neurons expressing the substance P receptor," *Science* (1997) 278: 275–279.

Theuer, Charles P., "Immunotoxins made with a recombinant form of *Pseudomonas* exotoxin A that do not require proteolysis for activity," *Cancer Research* (1993) 53: 340–347.

Wiley, R.G., et al., "Destruction of neurokinin–1 receptor expressing cells in vitro and in vivo using substance P–saporin in rats," *Neuroscience Letters* (1997) 230: 97–100.

* cited by examiner

SEQUENCE LISTING

```
<160> NUMBER OF SEQ ID NOS: 6

<210> SEQ ID NO 1
<211> LENGTH: 85
<212> TYPE: PRT
<213> ORGANISM: Artificial Sequence
<220> FEATURE:
<223> OTHER INFORMATION: Description of Artificial Sequence:exemplary
      Pseudomonas exotoxin translocation domain (domain II), residues
      280-364 of SEQ ID NO:6, except initiating Met in place of Gly at
      residue 280

<400> SEQUENCE: 1

Met Trp Glu Gln Leu Glu Gln Cys Gly Tyr Pro Val Gln Arg Leu Val
 1               5                  10                  15

Ala Leu Tyr Leu Ala Ala Arg Leu Ser Trp Asn Gln Val Asp Gln Val
             20                  25                  30

Ile Arg Asn Ala Leu Ala Ser Pro Gly Ser Gly Gly Asp Leu Gly Glu
         35                  40                  45

Ala Ile Arg Glu Gln Pro Glu Gln Ala Arg Leu Ala Leu Thr Leu Ala
     50                  55                  60

Ala Ala Glu Ser Glu Arg Phe Val Arg Gln Gly Thr Gly Asn Asp Glu
 65                  70                  75                  80

Ala Gly Ala Ala Asn
                 85

<210> SEQ ID NO 2
<211> LENGTH: 214
<212> TYPE: PRT
<213> ORGANISM: Artificial Sequence
<220> FEATURE:
<223> OTHER INFORMATION: Description of Artificial Sequence:exemplary
      Pseudomonas exotoxin ADP-ribosylation domain (domain III),
      residues 400-613 of SEQ ID NO:6

<400> SEQUENCE: 2

Phe Leu Gly Asp Gly Gly Asp Val Ser Phe Ser Thr Arg Gly Thr Gln
 1               5                  10                  15

Asn Trp Thr Val Glu Arg Leu Leu Gln Ala His Arg Gln Leu Glu Glu
             20                  25                  30

Arg Gly Tyr Val Phe Val Gly Tyr His Gly Thr Phe Leu Glu Ala Ala
         35                  40                  45

Gln Ser Ile Val Phe Gly Gly Val Arg Ala Arg Ser Gln Asp Leu Asp
     50                  55                  60

Ala Ile Trp Arg Gly Phe Tyr Ile Ala Gly Asp Pro Ala Leu Ala Tyr
 65                  70                  75                  80

Gly Tyr Ala Gln Asp Gln Glu Pro Asp Ala Arg Gly Arg Ile Arg Asn
             85                  90                  95

Gly Ala Leu Leu Arg Val Tyr Val Pro Arg Ser Ser Leu Pro Gly Phe
            100                 105                 110

Tyr Arg Thr Ser Leu Thr Leu Ala Ala Pro Glu Ala Ala Gly Glu Val
```

```
                    115                 120                 125
Glu Arg Leu Ile Gly His Pro Leu Pro Leu Arg Leu Asp Ala Ile Thr
    130                 135                 140

Gly Pro Glu Glu Gly Gly Arg Leu Glu Thr Ile Leu Gly Trp Pro
145                 150                 155                 160

Leu Ala Glu Arg Thr Val Val Ile Pro Ser Ala Ile Pro Thr Asp Pro
                165                 170                 175

Arg Asn Val Gly Gly Asp Leu Asp Pro Ser Ser Ile Pro Asp Lys Glu
            180                 185                 190

Gln Ala Ile Ser Ala Leu Pro Asp Tyr Ala Ser Gln Pro Gly Lys Pro
        195                 200                 205

Pro Arg Glu Asp Leu Lys
    210

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence:human
      Substance P (SP)

<400> SEQUENCE: 3

Arg Pro Lys Pro Gln Gln Phe Phe Gly Leu Met
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence:modified SP
      peptide with Cys added to amino terminus

<400> SEQUENCE: 4

Cys Arg Pro Lys Pro Gln Gln Phe Phe Gly Leu Met
1               5                   10

<210> SEQ ID NO 5
<211> LENGTH: 1839
<212> TYPE: DNA
<213> ORGANISM: Pseudomonas aeruginosa
<220> FEATURE:
<221> NAME/KEY: CDS
<222> LOCATION: (1)..(1839)
<223> OTHER INFORMATION: exotoxin A

<400> SEQUENCE: 5 gcc gaa gaa gct ttc gac ctc tgg aac gaa tgc gcc aaa gcc tgc gtg     48
Ala Glu Glu Ala Phe Asp Leu Trp Asn Glu Cys Ala Lys Ala Cys Val
1               5                   10                  15 ctc gac ctc aag gac ggc gtg cgt tcc agc cgc atg agc gtc gac ccg     96
Leu Asp Leu Lys Asp Gly Val Arg Ser Ser Arg Met Ser Val Asp Pro
            20                  25                  30 gcc atc gcc gac acc aac ggc cag ggc gtg ctg cac tac tcc atg gtc    144
Ala Ile Ala Asp Thr Asn Gly Gln Gly Val Leu His Tyr Ser Met Val
        35                  40                  45 ctg gag ggc ggc aac gac gcg ctc aag ctg gcc atc gac aac gcc ctc    192
Leu Glu Gly Gly Asn Asp Ala Leu Lys Leu Ala Ile Asp Asn Ala Leu
    50                  55                  60 agc atc acc agc gac ggc ctg acc atc cgc ctc gaa ggc ggc gtc gag    240
Ser Ile Thr Ser Asp Gly Leu Thr Ile Arg Leu Glu Gly Gly Val Glu
65                  70                  75                  80
```

| | |
|---|---|
| ccg aac aag ccg gtg cgc tac agc tac acg cgc cag gcg cgc ggc agt<br>Pro Asn Lys Pro Val Arg Tyr Ser Tyr Thr Arg Gln Ala Arg Gly Ser<br>              85                        90                      95 | 288 |
| tgg tcg ctg aac tgg ctg gta ccg atc ggc cac gag aag ccc tcg aac<br>Trp Ser Leu Asn Trp Leu Val Pro Ile Gly His Glu Lys Pro Ser Asn<br>            100                      105                      110 | 336 |
| atc aag gtg ttc atc cac gaa ctg aac gcc ggc aac cag ctc agc cac<br>Ile Lys Val Phe Ile His Glu Leu Asn Ala Gly Asn Gln Leu Ser His<br>              115                      120                    125 | 384 |
| atg tcg ccg atc tac acc atc gag atg ggc gac gag ttg ctg gcg aag<br>Met Ser Pro Ile Tyr Thr Ile Glu Met Gly Asp Glu Leu Leu Ala Lys<br>130                      135                    140 | 432 |
| ctg gcg cgc gat gcc acc ttc ttc gtc agg gcg cac gag agc aac gag<br>Leu Ala Arg Asp Ala Thr Phe Phe Val Arg Ala His Glu Ser Asn Glu<br>145                      150                    155                  160 | 480 |
| atg cag ccg acg ctc gcc atc agc cat gcc ggg gtc agc gtg gtc atg<br>Met Gln Pro Thr Leu Ala Ile Ser His Ala Gly Val Ser Val Val Met<br>              165                      170                    175 | 528 |
| gcc cag acc cag ccg cgc cgg gaa aag cgc tgg agc gaa tgg gcc agc<br>Ala Gln Thr Gln Pro Arg Arg Glu Lys Arg Trp Ser Glu Trp Ala Ser<br>            180                      185                    190 | 576 |
| ggc aag gtg ttg tgc ctc ctc gac ccg ctg gac ggg gtc tac aac tac<br>Gly Lys Val Leu Cys Leu Leu Asp Pro Leu Asp Gly Val Tyr Asn Tyr<br>              195                      200                    205 | 624 |
| ctc gcc cag caa cgc tgc aac ctc gac gat acc tgg gaa ggc aag atc<br>Leu Ala Gln Gln Arg Cys Asn Leu Asp Asp Thr Trp Glu Gly Lys Ile<br>210                      215                    220 | 672 |
| tac cgg gtg ctc gcc ggc aac ccg gcg aag cat gac ctg gac atc aaa<br>Tyr Arg Val Leu Ala Gly Asn Pro Ala Lys His Asp Leu Asp Ile Lys<br>225                      230                    235                  240 | 720 |
| ccc acg gtc atc agt cat cgc ctg cac ttt ccc gag ggc ggc agc ctg<br>Pro Thr Val Ile Ser His Arg Leu His Phe Pro Glu Gly Gly Ser Leu<br>              245                      250                    255 | 768 |
| gcc gcg ctg acc gcg cac cag gct tgc cac ctg ccg ctg gag act ttc<br>Ala Ala Leu Thr Ala His Gln Ala Cys His Leu Pro Leu Glu Thr Phe<br>            260                      265                    270 | 816 |
| acc cgt cat cgc cag ccg cgc ggc tgg gaa caa ctg gag cag tgc ggc<br>Thr Arg His Arg Gln Pro Arg Gly Trp Glu Gln Leu Glu Gln Cys Gly<br>              275                      280                    285 | 864 |
| tat ccg gtg cag cgg ctg gtc gcc ctc tac ctg gcg gcg cgg ctg tcg<br>Tyr Pro Val Gln Arg Leu Val Ala Leu Tyr Leu Ala Ala Arg Leu Ser<br>290                      295                    300 | 912 |
| tgg aac cag gtc gac cag gtg atc cgc aac gcc ctg gcc agc ccc ggc<br>Trp Asn Gln Val Asp Gln Val Ile Arg Asn Ala Leu Ala Ser Pro Gly<br>305                      310                    315                  320 | 960 |
| agc ggc ggc gac ctg ggc gaa gcg atc cgc gag cag ccg gag cag gcc<br>Ser Gly Gly Asp Leu Gly Glu Ala Ile Arg Glu Gln Pro Glu Gln Ala<br>              325                      330                    335 | 1008 |
| cgt ctg gcc ctg acc ctg gcc gcc gcc gag agc gag cgc ttc gtc cgg<br>Arg Leu Ala Leu Thr Leu Ala Ala Ala Glu Ser Glu Arg Phe Val Arg<br>            340                      345                    350 | 1056 |
| cag ggc acc ggc aac gac gag gcc ggc gcg gcc aac gcc gac gtg gtg<br>Gln Gly Thr Gly Asn Asp Glu Ala Gly Ala Ala Asn Ala Asp Val Val<br>              355                      360                    365 | 1104 |
| agc ctg acc tgc ccg gtc gcc gcc ggt gaa tgc gcg ggc ccg gcg gac<br>Ser Leu Thr Cys Pro Val Ala Ala Gly Glu Cys Ala Gly Pro Ala Asp<br>370                      375                    380 | 1152 |
| agc ggc gac gcc ctg ctg gag cgc aac tat ccc act ggc gcg gag ttc<br>Ser Gly Asp Ala Leu Leu Glu Arg Asn Tyr Pro Thr Gly Ala Glu Phe | 1200 |

```
                385                 390                 395                 400
ctc ggc gac ggc ggc gac gtc agc ttc agc acc cgc ggc acg cag aac           1248
Leu Gly Asp Gly Gly Asp Val Ser Phe Ser Thr Arg Gly Thr Gln Asn
                    405                 410                 415 tgg acg gtg gag cgg ctg ctc cag gcg cac cgc caa ctg gag gag cgc           1296
Trp Thr Val Glu Arg Leu Leu Gln Ala His Arg Gln Leu Glu Glu Arg
                420                 425                 430 ggc tat gtg ttc gtc ggc tac cac ggc acc ttc ctc gaa gcg gcg caa           1344
Gly Tyr Val Phe Val Gly Tyr His Gly Thr Phe Leu Glu Ala Ala Gln
            435                 440                 445 agc atc gtc ttc ggc ggg gtg cgc gcg cgc agc cag gac ctc gac gcg           1392
Ser Ile Val Phe Gly Gly Val Arg Ala Arg Ser Gln Asp Leu Asp Ala
        450                 455                 460 atc tgg cgc ggt ttc tat atc gcc ggc gat ccg gcg ctg gcc tac ggc           1440
Ile Trp Arg Gly Phe Tyr Ile Ala Gly Asp Pro Ala Leu Ala Tyr Gly
465                 470                 475                 480 tac gcc cag gac cag gaa ccc gac gca cgc ggc cgg atc cgc aac ggt           1488
Tyr Ala Gln Asp Gln Glu Pro Asp Ala Arg Gly Arg Ile Arg Asn Gly
                485                 490                 495 gcc ctg ctg cgg gtc tat gtg ccg cgc tcg agc ctg ccg ggc ttc tac           1536
Ala Leu Leu Arg Val Tyr Val Pro Arg Ser Ser Leu Pro Gly Phe Tyr
                    500                 505                 510 cgc acc agc ctg acc ctg gcc gcg ccg gag gcg gcg ggc gag gtc gaa           1584
Arg Thr Ser Leu Thr Leu Ala Ala Pro Glu Ala Ala Gly Glu Val Glu
                515                 520                 525 cgg ctg atc ggc cat ccg ctg ccg ctg cgc ctg gac gcc atc acc ggc           1632
Arg Leu Ile Gly His Pro Leu Pro Leu Arg Leu Asp Ala Ile Thr Gly
            530                 535                 540 ccc gag gag gaa ggc ggg cgc ctg gag acc att ctc ggc tgg ccg ctg           1680
Pro Glu Glu Glu Gly Gly Arg Leu Glu Thr Ile Leu Gly Trp Pro Leu
545                 550                 555                 560 gcc gag cgc acc gtg gtg att ccc tcg gcg atc ccc acc gac ccg cgc           1728
Ala Glu Arg Thr Val Val Ile Pro Ser Ala Ile Pro Thr Asp Pro Arg
                565                 570                 575 aac gtc ggc ggc gac ctc gac ccg tcc agc atc ccc gac aag gaa cag           1776
Asn Val Gly Gly Asp Leu Asp Pro Ser Ser Ile Pro Asp Lys Glu Gln
                    580                 585                 590 gcg atc agc gcc ctg ccg gac tac gcc agc cag ccc ggc aaa ccg ccg           1824
Ala Ile Ser Ala Leu Pro Asp Tyr Ala Ser Gln Pro Gly Lys Pro Pro
                595                 600                 605 cgc gag gac ctg aag                                                       1839
Arg Glu Asp Leu Lys
    610

<210> SEQ ID NO 6
<211> LENGTH: 613
<212> TYPE: PRT
<213> ORGANISM: Pseudomonas aeruginosa

<400> SEQUENCE: 6

Ala Glu Glu Ala Phe Asp Leu Trp Asn Glu Cys Ala Lys Ala Cys Val
  1               5                  10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
```

-continued

```
             65                  70                  75                  80
Pro Asn Lys Pro Val Arg Tyr Ser Tyr Thr Arg Gln Ala Arg Gly Ser
                     85                  90                  95
Trp Ser Leu Asn Trp Leu Val Pro Ile Gly His Glu Lys Pro Ser Asn
            100                 105                 110
Ile Lys Val Phe Ile His Glu Leu Asn Ala Gly Asn Gln Leu Ser His
            115                 120                 125
Met Ser Pro Ile Tyr Thr Ile Glu Met Gly Asp Glu Leu Leu Ala Lys
            130                 135                 140
Leu Ala Arg Asp Ala Thr Phe Phe Val Arg Ala His Glu Ser Asn Glu
145                 150                 155                 160
Met Gln Pro Thr Leu Ala Ile Ser His Ala Gly Val Ser Val Val Met
            165                 170                 175
Ala Gln Thr Gln Pro Arg Arg Glu Lys Arg Trp Ser Glu Trp Ala Ser
            180                 185                 190
Gly Lys Val Leu Cys Leu Leu Asp Pro Leu Asp Gly Val Tyr Asn Tyr
            195                 200                 205
Leu Ala Gln Gln Arg Cys Asn Leu Asp Asp Thr Trp Glu Gly Lys Ile
            210                 215                 220
Tyr Arg Val Leu Ala Gly Asn Pro Ala Lys His Asp Leu Asp Ile Lys
225                 230                 235                 240
Pro Thr Val Ile Ser His Arg Leu His Phe Pro Glu Gly Gly Ser Leu
            245                 250                 255
Ala Ala Leu Thr Ala His Gln Ala Cys His Leu Pro Leu Glu Thr Phe
            260                 265                 270
Thr Arg His Arg Gln Pro Arg Gly Trp Glu Gln Leu Glu Gln Cys Gly
            275                 280                 285
Tyr Pro Val Gln Arg Leu Val Ala Leu Tyr Leu Ala Ala Arg Leu Ser
            290                 295                 300
Trp Asn Gln Val Asp Gln Val Ile Arg Asn Ala Leu Ala Ser Pro Gly
305                 310                 315                 320
Ser Gly Gly Asp Leu Gly Glu Ala Ile Arg Glu Gln Pro Glu Gln Ala
            325                 330                 335
Arg Leu Ala Leu Thr Leu Ala Ala Glu Ser Glu Arg Phe Val Arg
            340                 345                 350
Gln Gly Thr Gly Asn Asp Glu Ala Gly Ala Ala Asn Ala Asp Val Val
            355                 360                 365
Ser Leu Thr Cys Pro Val Ala Ala Gly Glu Cys Ala Gly Pro Ala Asp
            370                 375                 380
Ser Gly Asp Ala Leu Leu Glu Arg Asn Tyr Pro Thr Gly Ala Glu Phe
385                 390                 395                 400
Leu Gly Asp Gly Gly Asp Val Ser Phe Ser Thr Arg Gly Thr Gln Asn
            405                 410                 415
Trp Thr Val Glu Arg Leu Leu Gln Ala His Arg Gln Leu Glu Glu Arg
            420                 425                 430
Gly Tyr Val Phe Val Gly Tyr His Gly Thr Phe Leu Glu Ala Ala Gln
            435                 440                 445
Ser Ile Val Phe Gly Gly Val Arg Ala Arg Ser Gln Asp Leu Asp Ala
            450                 455                 460
Ile Trp Arg Gly Phe Tyr Ile Ala Gly Asp Pro Ala Leu Ala Tyr Gly
465                 470                 475                 480
Tyr Ala Gln Asp Gln Glu Pro Asp Ala Arg Gly Arg Ile Arg Asn Gly
            485                 490                 495
```

```
Ala Leu Leu Arg Val Tyr Val Pro Arg Ser Ser Leu Pro Gly Phe Tyr
            500                 505                 510

Arg Thr Ser Leu Thr Leu Ala Ala Pro Glu Ala Ala Gly Glu Val Glu
        515                 520                 525

Arg Leu Ile Gly His Pro Leu Pro Leu Arg Leu Asp Ala Ile Thr Gly
        530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
                580                 585                 590

Ala Ile Ser Ala Leu Pro Asp Tyr Ala Ser Gln Pro Gly Lys Pro Pro
            595                 600                 605

Arg Glu Asp Leu Lys
            610
```

DISULFIDE CONJUGATED CELL TOXINS AND METHODS OF MAKING AND USING THEM

CROSS REFERENCE TO RELATED APPLICATIONS

The present application claims benefit of priority of U.S. Provisional Application No. 60/161,159 filed Oct. 22, 1999, which is herein incorporated by reference.

FIELD OF THE INVENTION

This invention generally pertains to the field of medicine and pain control. In particular, this invention pertains to the discovery of novel disulfide linked cell toxins which can ablate neurokinin-1 (NK-1) receptor expressing cells. These toxins are particularly useful as pharmaceutical for the treatment of chronic pain.

BACKGROUND OF THE INVENTION

NK-1 receptor expressing cells are expressed on a variety of cell types. Thus, ablation of these cells can be a means to treat a variety of condition of modulate many different physiologic processes. For example, while pain-mediating cells and neurons are the predominant cells expressing NK-1 receptors (e.g., spiral cord dorsal horn neurons, see e.g., Basbaum (1999) Reg. Anesth. Pain Med. 24:59–67 ; brain cells, see, e.g., Saria (1999) Eur. J. Pharmacol. 375:51–60; neostriatum cells through the axon collarterals of spiny projection neurons, see, e.g., Galarraga (1999) Synapse 33:26–35), a variety of other cells also express NK-1 receptors. Thus, although pain relief is a major result of the killing of NK-1 receptor expressing cells, many other conditions can also be treated. For example, spinal NK-1 receptors modulate autonomic reflexes, including the micturition reflex. In the peripheral nervous system, NK-1 receptors are widely expressed in the respiratory, genitourinary and gastrointestinal tracts. NK-1 receptors are also expressed by several types of inflammatory and immune cells. In the cardiovascular system, NK-1 receptors mediate endothelium-dependent vasodilation and plasma protein extravasation. At respiratory level, NK-1 receptors mediate neurogenic inflammation which is especially evident upon exposure of the airways to irritants. In the carotid body, NK-1 receptors mediate the ventilatory response to hypoxia. In the gastrointestinal system, NK-1 receptors mediate smooth muscle contraction, regulate water and ion secretion and mediate neuro-neuronal communication. In the genitourinary tract, NK-1 receptors are widely distributed in the renal pelvis, ureter, urinary bladder and urethra and mediate smooth muscle contraction and inflammation in response to noxious stimuli. NK-1 receptors antagonists, including toxins that can ablate NK-1 receptor expressing cells, may have several therapeutic applications at sites in both the central and peripheral nervous systems and tissues of the body. In the central nervous system, NK-1 receptor ablation toxins could be used to produce analgesia, as antiemetics and for treatment of certain forms of urinary incontinence due to detrusor hyperreflexia. In the peripheral nervous system, toxins of the invention could be used in several inflammatory diseases including arthritis, inflammatory bowel diseases and cystitis (Quartara (1998) Neuropeptides 32:1–49). Thus, there exists a need to develop a wide variety of NK-1 expressing cell toxins for use as treatments for a variety of different conditions and as modifiers of a variety of different physiologic mechanisms.

Toxins which kill NK-1 expressing cells can be used to treat pain. In particular deman are toxins which can treat chronic pain while at the same time not significantly affecting the ability to react to acutely painful, potentially dangerous, stimuli. Efforts to find more effective treatments of chronic pain which have few unwanted side effects or which do not dampen acutely painful potentially dangerous stimuli remains a continuing challenge. Current analgesic therapies often fall short of therapeutic goals and typically have unacceptable side effects. In many chronic pain syndromes, such as those subsequent to neuropathic injury, pain is not well controlled by any currently available method. Furthermore, most chronic pain treatment regimes affect the patient's ability to perceive acute pain, thus blunting or abrogating necessary protective basal nociceptive responses. Thus, the discovery of more efficacious and safe means to control chronic pain is unpredictable and therapeutically advantageous.

An endogenous peptide ligand of NK-1 receptors is the eleven amino acid long peptide Substance P ("SP'). SP plays a central role in pain signaling by possibly transducing second messenger signals from primary afferent nociceptive terminals to second-order neurons in the spinal cord (see, e.g., Lembeck (1981) Neuropeptides 1:175–180). SP transduces a pain signal by interacting primarily with NK-1 receptor-bearing cells in the brain and spinal chord (see, e.g., Abbadie (1996) Neuroscience 70:201–209). Thus, one strategy to control pain has involved making SP antagonists or SP-based toxins that can selectively kill NK-1 receptor-bearing cells (see, e.g., Iadarola (1997) Science 278:239–240; Fitzgerald, D., pp. 69 to 82, *In Towards a new Pharmacotherapy of Pain*, Ed. A. I. Basbaum et al., John Wiley & Sons Ltd. 1991). For example, Goettl, et al. inhibited a pain response in mice by intrathecal administration of an SP antagonist (Goettl (1998) Brain Res. 780:80–85). Fisher et al. demonstrated that a diptheria toxin-SP recombinant protein selectively killed cultured cells stably transfected with and expressing NK-1 receptors (Fisher (1996) Neurobiol. 93:7344–7345). One group injected rats intrathecally with a saporin toxin-SP disulfide-linked conjugate. This conjugate killed NK-1 receptor bearing cells in the superficial lamina I of the spinal cord and reduced chronic but not acute pain sensation (Mantyh (1997) Science 278:275–279; Wiley (1997) Neurosci. Letters 230:97–100). Benoliel et al. selectively killed NK-1 receptor-bearing cells to reduce chronic pain in a rat animal model by intrathecal administration of an SP/diptheria toxin recombinant protein. The recombinant protein killed NK-1 receptor-bearing cells and significantly reduced chronic pain as compared to acute pain (Benoliel (1999) Pain 79:243–253). Thus, because of the potential for treating the very refractive and unpredictable condition of chronic pain, new NK-1 receptor bearing cell toxins are needed.

In summary, there exists a need to develop a wide variety of NK-1 expressing cell toxins for use as treatments for a variety of different conditions and as modifiers of a variety of different physiologic mechanisms, particularly in the unpredictable field of chronic pain control. It is also extremely important to provide patients with end stage disease proper palliative care and new mediations for control of severe intractable pain are needed for this population.

SUMMARY OF THE INVENTION

The invention provides a method of making a cell toxin comprising reacting a polypeptide comprising a *Pseudomonas* exotoxin translocation domain linked to a *Pseudomonas* exotoxin ADP-ribosylation domain, wherein the Pseudomonas exotoxin translocation domain comprises at least one reactive sulfhydryl group, with a substance P peptide comprising one additional cysteine residue at its amino terminal end, wherein the cysteine sulfydryl group is disulfide linked to a di-thiobis (2-nitro)-benzoic acid group, such that after the reaction a disulfide bond is formed between the exotoxin polypeptide and the substance P and a thionitrobenzoate group is released, and purifying the substance P-*Pseudomonas* exotoxin disulfide linked conjugate from the released thionitrobenzoate group such that the purified conjugate is substantially free of thionitrobenzoate groups. In this method the *Pseudomonas* exotoxin translocation domain sulfhydryl group can be located within ten amino acid residues of the amino terminus or at the amino terminus. The *Pseudomonas* exotoxin translocation domain sulfhydryl group can be a cysteine residue or an equivalent, e.g., a peptidomimetic, an analog, a conservative substitution variation. The *Pseudomonas* exotoxin translocation domain can be covalently linked to the *Pseudomonas* exotoxin ADP-ribosylation domain, for example, the covalent linkage between the *Pseudomonas* exotoxin translocation domain and the *Pseudomonas* exotoxin ADP-riboslyation domain can be a peptide bond, or equivalent structure, as discussed below. The *Pseudomonas* exotoxin translocation domain can comprise an amino acid sequence as set forth in SEQ ID NO:1. The *Pseudomonas* exotoxin ADP-riboslyation domain can comprise an amimo acid sequence as set forth in SEQ ID NO:2.

The invention also provides a pharmaceutical composition for the ablation of NK1 receptor expressing cells. The pharmaceutical composition comprises a cell toxin and a pharmaceutically acceptable excipient, wherein the cell toxin is a substance P-*Pseudomonas* exotoxin disulfide linked conjugate made by a process comprising the following steps: reacting a polypeptide comprising a *Pseudomonas* exotoxin translocation domain linked to a *Pseudomonas* exotoxin ADP-riboslyation domain, wherein the *Pseudomonas* exotoxin translocation domain comprises at least one reactive sulfhydryl group, with a substance P peptide comprising one additional cysteine residue at its amino terminal end, wherein the cysteine sulfhydryl group is disulfide linked to a di-thiobis (2-nitro)-benzoic acid group, such that after the reaction a disulfide bond is formed between the exotoxin polypeptide and the substance P and a thionitrobenozate group is released, and purifying the substance P-*Pseudomonas* exotoxin disulfide linked conjugate from the released thionitrobenzoate group such that the purified conjugate is substantially free of thionitrobenzoate groups. The *Pseudomonas* exotoxin translocation domain sulfhydryl group can located within ten amino acid residues of the amino terminus or it can be located at the amino terminus. The *Pseudomonas* exotoxin translocation domain sulfhydryl group can be a cysteine residue or equivalent residue, as discussed below. The *Pseudomonas* exotoxin translocation domain can covalently linked to the Pseudomonas exotoxin ADP-riboslyation domain, for example, the covalent linkage between the *Pseudomonas* exotoxin translocation domain and the *Pseudomonas* exotoxin ADP-riboslyation domain can be a peptide bond. The *Pseudomonas* exotoxin translocation domain can comprise an amino acid sequence as set forth in SEQ ID NO:1. The *Pseudomonas* exotoxin ADP-riboslyation domain can comprise an amino acid sequence as set forth in SEQ ID NO:2. The cell toxin and pharmaceutically acceptable excipient can be suitable for administration intrathecally, subdurally, directly into the brain parenchyma, intraventricularly, or directly into a tumor (or systemic administration) for treatment of cancer cells that express a receptor that binds to SP (e.g., NK-1 receptor).

The invention also provides a method for ablating an NK1 receptor expressing cell in a patient comprising administering a cell toxin in a pharmaceutically acceptable excipient in an amount sufficient to ablate an NK1 receptor expressing cell, wherein the cell toxin is a substance P-*Pseudomonas* exotoxin disulfide linked conjugate made by a process comprising the following steps: reacting a polypeptide comprising a *Pseudomonas* exotoxin translocation domain linked to a *Pseudomonas* exotoxin ADP-riboslyation domain, wherein the *Pseudomonas* exotoxin translocation domain comprises at least one reactive sulfhydryl group, with a substance P peptide comprising one additional cysteine residue at its amino terminal end, wherein the cysteine sulfhydryl group is disulfide linked to a di-thiobis (2-nitro)-benzoic acid group, such that after the reaction a disulfide bond is formed between the exotoxin polypeptide and the substance P and a thionitrobenzoate group is released, and purifying the substance P-Pseudomonas exotoxin disulfide linked conjugate from the released thionitrobenzoate group such that the purified conjugate is substantially free of thionitrobenzoate groups. The ablated NK1 receptor expressing cell can be dorsal horn cells, neostriatalcells or other brain parenchyma cells. The ablated NK1 receptor expressing cell can also be inflammatory or immune cells, respiratory cells, genitourinary cells or gastrointestinal tract cells or tumore cells that express a receptor that binds SP (e.g., NK-1 receptor).

The invention also provides a method of treating chronic pain without significantly affecting basal nociceptive responses comprising administering a cell toxin in a pharmaceutically acceptable excipient in an amount sufficient to treat chronic pain without significantly affecting basal nociceptive responses, wherein the cell toxin is a substance P-*Pseudomonas* exotoxin disulfide linked conjugate made by a process comprising the following steps: reacting a polypeptide comprising a Pseudomonas exotoxin translocation domain linked to a *Pseudomonas* exotoxin ADP-ribosylation domain, wherein the *Pseudomonas* exotoxin translocation domain comprises at least one reactive sulfhydryl group, with a substance P peptide comprising one additional cysteine residue at its amino terminal end, wherein the cysteine sulfhydryl group is disulfide linked to a di-thiobis (2-nitro)-benzoic acid group, such that after the reaction a disulfide bond is formed between the exotoxin polypeptide and the substance P and a thionitrobenzoate group is released, and purifying the substance P-*Pseudomonas* exotoxin disulfide linked conjugate from the released thionitrobenzoate group such that the purified conjugate is substantially free of thionitrobenzoate groups. The cell toxin can be administered, for example, in the form of a pharmaceutical composition, to epineurium cells, perineurium cells, nerve ganglia, nerve sheathes, nerve linings, meninges, pia mater cells, arachnoid membrane cells, dura membrane cells, cells lining a joint or brain or spinal cord parenchymal cells or tumor cells expressing the proper receptor. The pharmaceutical composition can be administered intrathecally or injected directly into spinal cord or brain parenchymal cells, or joint spaces, or intravenously. For example, the pharmaceutical composition can be delivered into the subarachnoid space through implanted or external intrathecal or epidural pumps.

A further understanding of the nature and advantages of the present invention is realized by reference to the remaining portions of the specification, the figures and claims.

All publications, patents and patent applications cited herein are hereby expressly incorporated by reference for all purposes.

DESCRIPTION OF THE INVENTION

Figure 1:
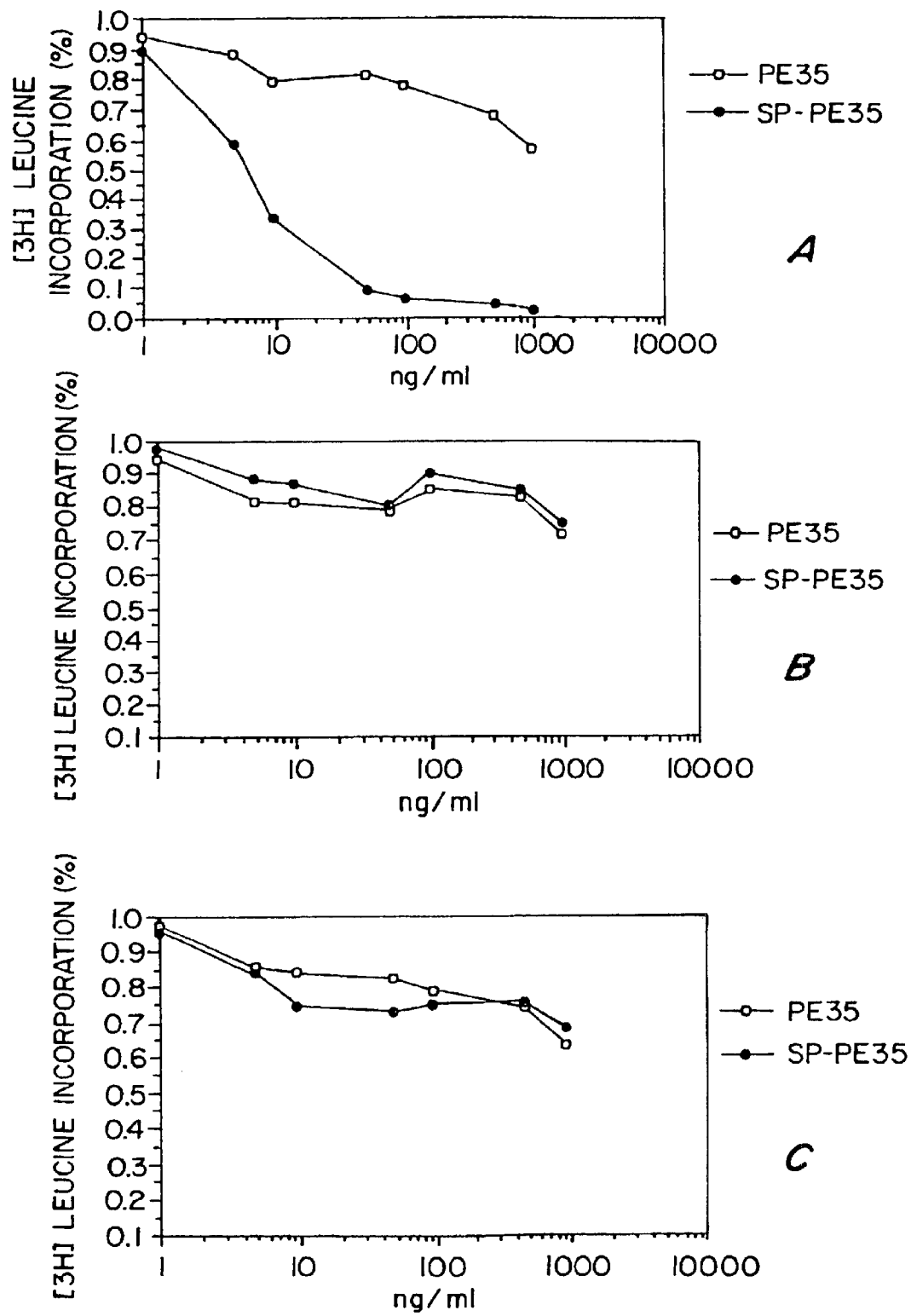
FIG. 1 shows a schematic summary of data of experiments testing the ability of the SP-PE conjugate toxin of the invention to kill CHO cells stably transfected with and expressing NK-1 receptors (FIG. 1A), NK-2 receptors (FIG. 1B), and NK-3 receptors (FIG. 1C), as discussed in detail in Example 1, below.

This invention is the discovery of a of a novel disulfide linked cell toxin conjugate comprising a modified substance P ("SP") peptide and a modified *Pseudomonas* exotoxin polypeptide. This novel cell toxin conjugate is particularly effective in ablating NK-1 receptor-expressing cells. Killing such cells in an effective means of treating a variety of conditions, particularly, chronic pain or tumors that express a receptor that binds SP, e.g., NK-1 receptors.

The SP-PE toxins of the invention of particularly efficacious in treating patients with end stage cancer and other long term diseases associated with chronic pain who often need greater levels of pain control than currently available drugs can provide. Because the SP-PE toxins of the invention only kill NK-1 receptor expressing cells, they can be used effectivly in combination, with conventional pain-killing drugs, e.g., opioids. The Examples below show that the SP-PE toxin of the invention only kills substance P receptor (NK-1 receptor)-expressing cells in the spinal cord but spares the opiod receptor expressing cells. Thus, the patient's capacity to be managed with opioids will not be impaired. Accordingly, the invention provides an advanced and improved pain management strategy that will provide greater pain relief. The needs of these chronic and severe pain patients are underserved and the toxins of the invention can be used to provide an additional level of palliative care by selectively deleting key components in the pain transmission circuit.

Furthermore, in animal model studies, appropriate doses of SP-PE can also block basal nociceptive responses without overtly impairing other functions such as locomotion. The fact that the toxin of the invention can be administered to alleviate pain without detectable motoric involvement expands the possible uses of SP-PE, particularly in patients that have problems such as cancer pain. For example, the SP-PE toxin can be used in patients have a chronic disease that causes intermittant problems with the pain system but chronic pain is always present. For example, bone metastasis to the sacral spinal column in prostate cancer makes it very painful to sit and move. This type of "acute" pain can be very effectively treated with the SP-PE toxins of the invention, whereas other drugs fail routinely.

The modified *Pseudomonas* exotoxin ("PE") polypeptide comprises a *Pseudomonas* exotoxin cell translocation domain linked to a *Pseudomonas* exotoxin ADP-ribosylation domain. The *Pseudomonas* exotoxin translocation domain comprises at least one reactive sulfhydryl group; one exemplary translocation domain has only one cysteine group (or equivalent, e.g., a peptidomimetic); e.g., at the residue corresponding to position 287 of the naturally expressed PE, as described below.

The SP peptide used in the toxin conjugate of the invention comprises one additional cysteine residue (or equivalent, e.g., a peptidomimetic) at its amino terminal end. This amino terminal residue is disulfide linked to a di-thiobis (2-nitro)-benzoic acid group, or equivalent. After the reacting the modified PE (with only one active sulfhydryl group) and the modified SP together, a disulfide bond is formed between the exotoxin polypeptide and the SP. The reaction also results in release of a thionitrobenzoate (or equivalent, if used) group. This reaction results in a one to one molar basis between the disulfide linked SP and PE groups. The SP peptide is also amidated at its carboxy terminal amino acid residue (or equivalent), as discussed below.

The toxin conjugate is then purified from the released thionitrobenzoate group such that the purified conjugate is substantially free of thionitrobenzoate groups, i.e., the purified toxin conjugate preparation less than about 2% (on a molar basis) thionitrobenzoate groups remaining. Thus, the pharmaceutical compositions of the invention have less than 2% thionitrobenzoate. The invention also comprises toxin conjugate preparations that have less than 1% and 0.5%, and 0.25% "contaminating" thionitrobenzoate (or equivalent, if used) group.

In alternatively embodiments, in place of SP, neuropeptide FF, Neuropeptide Y, preproenkephalin derived peptides, preprodynorphin peptides, other tachykinin peptides, neurotensin, caclitonin gene related peptide and its fragments can be conjated to PE.

In studies described in the Examples, below, CHO cells stably transfected with and expressing NK-1 receptors, but not NK-2 or NK-3 receptors, were killed by the cell toxin conjugate of the invention. Toxicity to NK-1 receptor expressing cells was blocked by the addition of excess free SP or by treating the toxin conjugate with an anti-SP antibody. Cytotoxicity occurred with exposure times to toxin as short as a two minutes (lethality assessed at 24 hours after exposure). The toxin conjugate of the invention was extremely effective in deleting NK-1 receptor expressing cells from the dorsal horn of the spinal cord and NK-1 receptor expressing cells from the striatum. The data described in the Examples, below, demonstrate that the toxin conjugate of the invention can kill NK-1 receptor expressing cells, e.g., ablate neurons when administered into the cerebral spinal fluid space (CSF) and when administered directly into the brain parenchyma.

DEFINITIONS

Unless defined otherwise, all technical and scientific terms used herein have the meaning commonly understood by a person skilled in the art to which this invention belongs. As used herein, the following terms have the meanings ascribed to them unless specified otherwise.

The term "administering" incorporates the common usage and refers to any appropriate means to give a pharmaceutical to a patient, taking into consideration the pharmaceutical composition and the preferred site of administration (e.g., in a preferred embodiment, the pharmaceutical composition of the invention is injected into the subarachnoid space as an aqueous solution).

The term "basal nociceptive responses" incorporates its common usage and refers to baseline responses to nociceptive, or painful, stimuli.

The terms "chronic pain" and "acute pain" incorporate their common usages; subjective (e.g., clinical diagnosis)

and objective means (e.g., laboratory tests, PET) to determine the presence of chronic pain and/or acute pain, and to distinguish between these two distinct categories of pain, are described in detail, herein.

The term "pharmaceutically acceptable excipient" incorporates the common usages and includes any suitable pharmaceutical excipient, including, e.g., water, saline, phosphate buffered saline, Hank's solution, Ringer's solution, dextrose/saline, glucose, lactose, or sucrose solutions, magnesium stearate, sodium stearate, glycerol monostearate, glycerol, propylene glycol, ethanol, and the like.

The terms "polypeptide" and "peptide" including "*Pseudomonas* exotoxin translocation domain, "*Pseudomonas* exotoxin ADP-ribosylation domain" and "substance P" (or "SP") peptide includes polypeptides and peptides having an activity and a structural characteristic which substantially corresponds to their corresponding polypeptides. These include "analogs," "conservative variants," "peptidomimetics" and "mimetics" with structures and activity which substantially correspond to exemplary sequences. For example, an exemplary, modified *Pseudomonas* exotoxin translocation domain comprises an amino acid sequence as set forth in SEQ ID NO:1 (with only one cysteine residue, as discussed below) and an exemplary *Pseudomonas* exotoxin ADP-ribosylation domain comprises an amino acid sequence as set forth in SEQ ID NO:2 (residues 400 to 613 of SEQ ID NO:6). The amino acid sequences set forth in the present application use the conventional practice wherein the amino group is presented to the left (the N-terminus) and the carboxyl group to the right (the C-terminus) of each amino acid residue.

Human substance P ("SP") is an eleven amino acid peptide having the sequence RPKPQQFFGLM (SEQ ID NO:3). Naturally occuring SP is amidated on its carboxy terminus. The invention uses a modified twelve residue SP peptide—a cysteine residue (or equivalent) is added to the amino terminus; CRPKPQQFFGLM (SEQ ID NO:4), and, the carboxy terminal amino acid residue (or equivalent) is amidated (in one embodiment, the SP is made synthetically, amidated, conjugated to TNB and then disulfide linked to PE). The "polypepties" and "peptides" of the invention include "conservative variants" and "analogs" which have modified amino acid sequences such that the change(s) do not substantially alter the polypeptide's (the conservative variant's) structure and/or activity. Structural variations to the SP or PE moieties may advantageously alter potency, selectivity or stability to enzymatic degradation.

Thus, a substance P peptides or variants or mimetic thereof are within the scope of the invention if they are capable of binding to an NK-1 receptor expressed on a eukaryotic cell, such as a human cell (binding protocols for such determinations are well known in the art, see, e.g., Ciucci (1998) Br. J. Pharmacol. 125:303–401; Maguire (1998) Brain Res. 786:263–266). Alternatively, a non-natural residue (e.g., peptidomimetic) comprising a sulfhydryl or equivalent moiety can be designed to replace the cysteine on the N-terminus of the modified SP peptide used in the toxin conjugates of the invention.

*Pseudomonas* exotoxin translocation domain variants or mimetics thereof are within the scope of the invention if they are capable of translocating through an endosmal/microsmal membrane into the cytosol (means for such determinations are well known in the art, see e.g., Theuer (1994) Biochemstry 33:5894–5900). A *Pseudomonas* exotoxin ADP-ribosylation domain variant or mimetic thereof is within the scope of the invention if, after translocation to the cytosol, can inhibit protein synthesis by ADP-ribosylating elongation factor 2 (means for such determinations are well known in the art, see, e.g. Zdanovsky (1993) J. Biol. Chem. 268(29) :21791–21799; or, the method of Collier and Kandel, as described in Mansfield (1998)Bioconjugate Chem. 7:557–583, p. 558). The cell killing effectiveness of the cell toxin can be determined using any cytotoxicity assay, many of which are well known in the art (e.g., cell death quantitated using the MTT method of Mosmann (1983) J. Immunol. Meth. 65:55–63).

These include conservatively modified variations of an amino acid sequence, i.e., amino acid substitutions, additions or deletions of those residues that are not critical for protein or peptide activity, or substitution of amino acids with residues having similar properties (e.g., acidic, basic, positively or negatively charged, polar or non-polar, etc.) such that the substitutions of even critical amino acids does not substantially alter structure and/or activity. Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gln/asn; gly/asp; gly/ala or pro; his/asn or gln; ile/leu or val; leu/ile or val; lys/arg or gln or glu; met/leu or tyr or ile; phe/met or leu or tyr; ser/thr; thr/ser; trp/tyr; tyr/trp or phe; val/ile or leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucin (L), Methionine (M), Valine (V); and 6) Phenylalanine (F), Tyrosine (Y), Tryptophan (W); (see also, e.g., Creighton (1984) Proteins, W. H. Freeman and Company; Schulz and Schimer (1979) Principles of Protein Structure, Springer-Verlag). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions which alter, add or delete a single amino acid or a small percentage of amino acids in an encoded sequence can also be considered "conservatively modified variations." Routine experimentation will determine whether a conservative variant, analog, mimetic or the like is within the scope of the invention, i.e., that its structure and/or function is not substantially altered; exemplary means are well known, as described herein.

The terms "mimetic" and "peptidomimetic" refer to a synthetic chemical compound which has substantially the same structural and/or functional characteristics of the *Pseudomonas* exotoxin translocation domain, *Pseudomonas* exotoxin ADP-ribosylation domain and "SP" polypeptides and peptides of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants, routine experimentation (as discussed herein) will determine whether a mimetic is within the scope of the invention, i.e., that its structure and/or function is not substantially altered. Polypeptide mimetic compositions can contain any combination of nonnatural structural components, which are typically from three structural groups: a) residue linkage groups other than the natural amide bond ("peptide bond") linkages; b) nonnatural residues in place of naturally occurring amino acid residues; or c) residues which induce secondary structural mimiery, i.e., to induce or stabilize a secondary structure, e.g., a beat turn, gamma turn, beta sheet, alpha helix conformation, and the like.

The term "llinked" means polypeptide domains or individual residues are joined, "linked" by means other than natural peptide bonds. These include, e.g., electrostatic (e.g., ionic, van der Waals or hydrogen bonds) or chemical means. For example, the cell toxins of the invention comprise a *Pseudomonas* exotoxin translocation domain linked to a *Pseudomonas* exotoxin ADP-ribosylation domain. Polypeptide domains or individual peptidomimetic residues can be joined by peptide bonds or other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in Chemistry and Biochemistry of Amino Acids, Peptides and Proteins, Vol. 7, pp 267–357, "Peptide Backbone Modifications," Marcell Dekker, N.Y.).

A polypeptide can also be characterized as a mimetic by containing all or some non-natural residues in place of naturally occurring amino acid residues. Nonnatural residues are well described in the scientific and patent literature; a few exemplary nonnatural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenlyglycine; D-(trifluoromethyl)-phenylglycine; D-(trifluoromethyl) -phenylalanine; D-p-fluorophenylalanine; D- or L-p-biphenylphenylalanine; K- or L-p-methoxybiphenylphenylalanine; D- or L-2-indole (alkyl)alanines; and, D- or L-alkylainines, where alkyl can be substituted or unsubstituted methyl, ethyl, propyl, hexyl, butyl, pentyl isopropyl, iso-butyl, sec-isotyl, iso-pentyl, or a non-acidic amino acids. Aromatic rings of a nonnatural amino acid include, e.g., thiazolyl, thiophenyl, pyrazolyl, benzimidazolyl, naphthyl, furanyl, pyrrolyl, and pyridyl aromatic rings. Mimetics of acidic amino acids can be generated by substitution by, e.g., non-carboxylate amino acids while maintaining a negative charge; (phosphono) alanine; sulfated threonine. Carboxyl side groups (e.g., aspartyl or glutamyl) can also be selectively modified by reaction with carbodiimides (R'—N—C—N—R') such as, e.g., 1-cyclohexyl-3(2-morpholinyl-(4-ethyl) carbodiimide or 1-ethyl-3(4-azonia-4,4-dimetholpentyl)carbodiimide. Aspartyl or glutamyl can also be converted to asparaginyl and glutaminyl residues by reaction with ammonium ions. Mimetics of basic amino acids can be generation by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedoine, 1,2-cyclohexanedione, or ninhydrin, preferably under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3- nitro derivatives respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitro-benzenesulfonic acid, O-methylisourea, 2,4, pentanedione, and transamidase-catalyzed reactions with glyoxylate. Mimetics of methioninie can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3-dimethylproline. Histidine residue mimetics can be generated by reacting histidyl with, e.g., diethylprocarbonate or para-bromophenacyl bromide. Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A naturally occuring amino acid in a polypeptide or peptide of the invention can be replaced by a natural or synthetic amino acid of peptidomimetic residue of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but the opposite chirality, generally referred to as the D- amino acid, but which can additionally be referred to as the R- or S- form.

The mimetics of the invention can also include compositions that contain a structural mimetic residue, particularly a residue that induces or mimics secondary structures, such as a beta turn, beta sheet, alpha helix structures, gamma turns, and the like. For example, substitution of natural amino acid residues with D-amino acids; N-alpha-methyl amino acids; C-alpha-methyl amino acids; or dehydroamino acids within a peptide can induce or stabilize beta turns, gamma turns, beta sheets or alpha helix conformations. Beta turn mimetic structures have been described, e.g., by Nagai (1985) Tet. Lett. 26:647–650; Feigl (1986) J. Amer. Chem. Soc. 108:181–182; Kahn (1988) J. Amer. Chem. Soc.

110:1638–1639; Kemp (1988) Tet. Lett. 29:5057–5060; Kahn (1988) J. Molec. Recognition 1:75–79. Beta sheet mimetic structures have been described, e.g., by Smith (1992) J. Amer. Chem. Soc. 114:10672–10674. For example, a type VI beta turn induced by a cis amide surrogate, 1,5-disubstituted tetrazol, is described by Beusen (1995) Biopolymers 36:181–200. Incorporation of achiral omega-amino acid residues to generate polymethylene units as a substitution for amide bonds is described by Banerjee (1996) Biopolymers 39:769–777. Secondary structures of polypeptides can be analyzed by, e.g., high-field 1H NMR or 2D NMR spectroscopy, see. e.g., Higgins (1997) J. Pept. Res. 50:421–435. See also, Hruby (1997) Biopolymers 43:219–266, Balaji, et al., U.S. Pat. No. 5,612,895.

The skilled artisan will recognize that individual synthetic residues and polypeptides incorporating mimetics can be synthesized using a variety of procedures and methodologies, which are well described in the scientific and patent literature, e.g., Organic Syntheses Collective Volumes, Gilman et al. (Eds) John Wiley & Sons, Inc. N.Y. Polypeptides incorporating mimetics can also be made using solid phase synthetic procedures, as described, e.g., by Di Marchi, et al:, U.S. Pat. No. 5,422,426. Mimetics of the invention can also be synthesized using combinatorial methodologies. Various technique for generation of peptide and peptidomimetic libraries are well known, and include, e.g., multipin, tea bag, and split-couple-mix techniques; see, e.g., al-Obeidi (1998) Mol. Biotechnol, 9:205–223; Hruby (1997) Curr. Opin. Chem. Biol. 1.114–119; Ostergaard (1997) Mol. Divers. 3:17–27; Ostresh (1996) Methods Enzymol. 267:220–234.

The term "pia mater connective tissue" incorporates the common usage refers to the tissue, membrane, or connective tissue which separates the parenchyma of the spinal cord from the subarachnoid space (the cerebral spinal fluid (CSF) space).

The term "spinal cord parenchymal tissue" incorporates the common usage and refers to the body of the spinal cord containing nerve tissue, e.g., white and gray mater.

The term "subarachnoid space" or cerebral spinal fluid (CSF) space incorporates the common usage refers to the anatomic space between the pia mater and the arachnoid membrane containing CSF.

The term "substantially free of thionitrobenzoate groups" means that the toxin conjugate is then purified from the released thionitrobenzoate (or its equivalent, if used) group such that the purified conjugate is substantially free of thionitrobenzoate groups, i.e., the purified toxin conjugate preparation less than about 2% (on a molar basis) thionitrobenzoate (or equivalent) groups remaining. Thus, the pharamceutical compositions of the invention have less than 2% thionitrobenzoate. In alternative embodiments, toxin conjugate preparations (including pharmaceuticals of the invention) that have less than 1%, and 0.5%, and 0.25% "contaminating" thionitrobenzoate (or equivalent) group.

The term "treating" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; slowing in the rate of degeneration or decline; making the final point of degeneration less debilitating; improving a patient's physical or mental well-being; or, in some situations, preventing the onset of the symptom or condition, e.g., pain. The treatment or amelioration of symptoms can be based on any objective or subjective parameter; including, e.g., the result of a physical examination and/or a psychiatric evaluation, or, simply an improvement in the patient's sense of well-being. For example, the methods of the invention selectively treats chronic pain by ameliorating the hyperalgesia associated with chronic pain, while not significantly affecting basal nociceptive responses.

Distinguishing Chronic from Acute Pain

Pain is always subjective and can have physiologic, pathophysiologic, psychologic, emotional, and affective dimensions. Pain causation can be broadly categorized as organic or psychogenic. Basically, two types of pain exist— acute pain and chronic pain. Each possibly is mediated by anatomically different nerves. Each type of pain has a different physiologic role. For example, the ability to perceive and respond to "acutely" painful stimuli, which usually has the potential to cause tissue damage, serves a protective role for the individual. While many treatments for acute pain cannot ameliorate chronic pain (this, in face, is used as one means to objectively identify "chronic" versus "acute" pain, as discussed below), before this invention, there existed no effective therapies to treat chronic pain without the unwanted side effect of significantly dampening protective acute pain responses.

Diagnosing and Assessing Chronic Pain

The invention provides methods of treating chronic pain while at the same time not significantly affecting the ability to respond to acutely painful, and potentially harmful, stimuli. Thus, proper diagnosis of chronic pain aids in the practice and assessment of efficacy (e.g., for a particular dosage regimen or mode of administration) of the compositions and methods of the invention. Means to diagnosis chronic pain include classical clinical and psychological evaluations, which can be augmented by various laboratory procedures, as described herein. Such means as welldescribed in the medical/scientific and patent literature; some illustrative examples are provided below.

One criteria to diagnose a "chronic" pain is whether the pain persists for a month beyond the usual course of an acute disease or a reasonable time for an injury to heal. This evaluation is made by the clinician on a case by case basis. Acute diseases or injuries can heal in 2, 3, or at most, 6 weeks, depending on the nature of the condition or injury, the age and health of the patient, and the like. Clinicians are trained to be very aware of this "acute" versus "chronic" pain distinction, for it is critical to make correct diagnosis and treatment plans. For example, a simple wrist fracture can remain painful for a week to ten days; however, if pain persists longer than this period, a dystropathy could be developing which will be irreversible if not treated. See, e.g., Bonica, et al., (1990) "Management of Pain," 2nd Ed., Vol. I, Lea & Feibiger, Phil., Pa; Wall and Melzack (1994) "Textbook of Pain," Churchill Livingston, N.Y. Accordingly, a chronic pain is diagnosed by the practitioner based on clinical and laboratory results, depending on the particular condition or injury, patient, and the like (see also, e.g., Russo (1998) Annu. Rev. Med. 49:123–133).

Another means to identify a "chronic" pain is by diagnosis of a pathologic process (which is usually also chronic) known to produce or be associated with chronic pain. Such conditions are well characterized and include, e.g., chronic pain syndrome (see, e.g., Clifford (1993) Can. Fam. Physician 39:540–559), arthralgia, arthritis (e.g., osteoarthritis and rheumatoid arthritis), causalgia, hyperpathia, neuralgai, neuritis, radiculagia, fibromyalgia (see, e.g., Simms (1998) Am. J. Med. Sci. 315:346–350), orofacial pain and temporomandibular disorders (see, e.g., Binderman (1997) Curr. Opin. Periodontol. 4:144–15), reflex sympathetic dystrophy (see, e.g., Dangel (1998) Paediatr. Anaesth. 8:105–112, chronic back pain, certain cancers and the like.

Chronic pain is also associated with particular injuries to the nerves. These include, e.g., nerve transection (traumatic or surgical), chronic abnormal pressure on a nerve, chemical (e.g., formalin) destruction of nerve tissue, and the like.

Chronic pain can also be distinguished form acute pain by its non-responsiveness to pharmacologic therapies known to significantly ameliorate or abate acute pain. When pain is initially diagnosed as acute or of unknown etiology, the clinician typically administers one of several analgesics known in the art to be effective for acute pain, such as e.g., a non-steroid anti-inflammatory drug (NSAID), such as, e.g., aspirin, ibuprofen, propoxyphene, tramadol, acetaminophen and the like (see, e.g., Tramer (1998) Acta Anaesthesiol. Scand. 42:71–79). If there is no significant amelioration of pain, as assessed by the clinician, over an approximately six week period, then a provisional diagnosis of chronic pain can be made. Ultimately, as discussed above, a diagnosis of chronic pain depends upon determination as to whether pain would be expected, given each individual situation.

Other treatments to which chronic pain is also typically incompletely or totally unresponsive include tricyclic antidepressant administration, psychotherapy, or alternative medicines, such as acupuncture, biofeedback, and the like.

Laboratory, radiographic and other types of imaging procedures can also be used to diagnose chronic pain. In particular, positron emission tomography, or PET, now allows the clinician to objectify such otherwise merely subjective symptoms, including chronic pain (see, e.g., Reiss (1998) Fortschr. Med. 116:40–43; Di Piero (1991) Pain 46:9–12).

SP Peptides and PE Polypeptides Domains

The invention provides pharmaceutical compositions comprising polypeptides cell toxins in an pharmaceutically acceptable excipient. The invention also provides methods of making and using these pharmaceutical compositions to treat to treat a variety of conditions responsive to the ablation of NK-1 receptor expressing cell, e.g., chronic pain. The invention can be practiced in conjunction with any method or protocol known in the art, which are well described in the scientific and patent literature. Therefore, only a few general techniques will be described prior to discussing specific methodologies and examples relative to the novel reagents and methods of the invention.

GENERAL TECHNIQUES

The polypeptide domains and peptides which comprise the cell toxin conjugates of the invention can be genetically engineered and/or expressed recombinantly. Techniques for the manipulation of nucleic acids, such as, e.g., subcloning into expression vectors, labeling probes, sequencing DNA, DNA hybridization are described in the scientific and patent literature, see e.g., Sambrook, ed., MOLECULAR CLONING: A LABORATORY MANUAL (2ND ED.), Vols. 1–3, Cold Spring Harbor Laboratory, (1989) ("Sambrook"); CURRENT PROTOCOLS IN MOLECULAR BIOLOGY, Ausubel, ed. John Wiley & Sons, Inc., New York (1997) ("Ausubel"); and, LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993) ("Tijssen"). Product information from manufactures of biological reagents and experimental equipment also provide information regarding known biological methods. Nucleic acids can also be generated or quantitated using amplification techniques. Suitable amplification methods include, but are not limited to: polymerase chain reaction, PCR (PCR PROTOCOLS, A GUIDE TO METHDOS AND APPLICATIONS, ed. Innis, Academic Press, N.Y. (1990), ligase chain reaction (LCR) (Barringer (1990) Gene 89:117); and the like.

Alternatively, peptides and polypeptides domains used to practice the invention can be chemically synthesized in vitro, whole or in part, using chemical methods well known in the art; see e.g., Caruthers (1980) Nucleic Acids Res. Symp. Ser. 215–223; Horn (1980) Nucleic Acids Res. Symp. Ser. 225–232; Banga, A. K., Therapeutic Peptides and Proteins, Formulation, Processing and Delivery Systems (1995) Technomic Publishing Co., Lancaster, Pa. ("Banga"). For example, peptide synthesis can be performed using various solid-phase techniques (see e.g., Roberge (1995) Science 269:202; Merrifield (1997) Methods Enzymol. 289:3–13) and automated synthesis may be achieved, e.g., using the ABI 431A Peptide Synthesizer (Perkin Elmer) in accordance with the instructions provided by the manufacturer.

The skilled artisan will recognize that individual synthetic residues and polypeptides incorporating mimetics can be synthesized using a variety of procedures and methodologies, which are well described in the scientific and patent literature, e.g., Organic Syntheses Collective Volumes, Gilman, et al. (Eds) John Wiley & Sons, Inc., N.Y. Polypeptides incorporating mimetics can also be made using solid phase synthetic procedures, as described, e.g., by Di Marchi, et al., U.S. Pat. No. 5,422,426. Peptides and peptide mimetics of the invention can also be synthesized using combinatorial methodologies. Various techniques for generation of peptide and peptidomimetic libraries are well known, and include, e.g., multipin, tea bag, and split-couple-mix techniques; see, e.g., al-Obeidi (1998) Mol. Biotechnol. 9:205–223; Hruby (1997) Curr. Opin. Chem. Biol. 1:114–119; Ostergaard (1997) Mol. Divers. 3:17–27; Ostresh (1996) Methods Enzymol. 267:220–234. Modified peptides of the invention can be further produced by chemical modification methods, see, e.g., Belousov (1997) Nucleic Acids Res. 25:3440–3444; Frenkel (1995) Free Radic. Biol. Med. 19:373–380; Blommers (1994) Biochemistry 33:7886–7896.

Nucleic acids, peptides and proteins, analogs and mimetics thereof, can be detected and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatogrpahy, various immunological methods, such as fluid or gel precipitin reactions, immunodiffusion (single or double), immunoelectrophoresis, radioimmunoassays (RIAs), enzyme-linked immunosorbent assays (ELISAs), immunofluorescent assays, Southern analysis, northern analysis, Dot-blot analysis, gel electrophoresis (e.g., SDS-PAGE), RT-PCR, quantitative PCR, other nucleic acid or target or signal amplification methods, radiolabeling, scintillation counting, and affinity chromatography.

*Pseudomonas* exotoxin A

Following SP-NK-1 receptor binding on the cell surface, the ligand-receptor complex is internalized. This makes the NK-1 receptor a rational target for toxin-derived therapeutics. *Pseudomonas* exotoxin is a member of a protein family functionally characterized and a "reverse internalized predator." Toxins in this class act in the cytosol of mammalian cells to inhibit protein synthesis and cause cell death at very low concentrations. These toxins use the endocytosis pathway to gain entry to intracellular sorting vesicles, where they unfold and translocated into the cytosol. After translocation they refold and enzymatically inhibit protein synthesis. Because of high enzymatic catalytic rates and apparent resistance of these toxins to proteosome degradation, only one or a few molecules need to reach to cytosol to be effective.

Naturally expressed *Pseudomonas* exotoxin A can be used as a model to design toxin polypeptide domains to be used in the toxin conjugates of the invention. The naturally expressed toxin is secreted by *Pseudomonas* aeruginosa as a 67 kD protein composed of three prominent globular domains, termed Ia, II, and III. A small subdomain, termed Ib, connects domains II and III (see, e.g., Allured (1986) Proc. Natl. Acad. Sci. 83:1320–1324).

Domain Ia of PE mediates cell binding. In nature, domain Ia binds to the low density lipoprotein receptor-related protein ("LRP"), also known as the α2-macroglobulin receptor ("α2-MR") (see, e.g., Kounnas (1992) J. Biol. Chem. 267:12420–23). Domain Ia of PE spans amino acids residues 1 to 252. While cell toxin conjugates of the invention lack a functional PE cell binding domain (replaced by SP in the conjugate), some residues of this domain may remain in the polypeptide comprising the *Pseudomonas* exotoxin translocation domain linked to a *Pseudomonas* exotoxin ADP-ribosylation domain.

The *Pseudomonas* exotoxin translocation domain, or domain II, mediates translocation of the polypeptide from the endosome/microsome to the cytosol. Domain II spans amino acids 253 to 364 in naturally occurring PE (see SEQ ID NO:6, below). An amino acid domain sufficient to effect translocation can be derived from the translocation domain of native PE. The translocation domain can include the entire sequence of domain II. However, the entire sequence is not necessary for translocation. For example, the amino acid sequence can minimally contain, e.g., amino acids 280–344 (see SEQ ID NO:6, below) of domain II of PE. Sequences outside this region, i.e., amino acids 253–279 and/or 345–364, can be eliminated from the domain. This domain also can be engineered with substitutions, analogs, mimetic, and the like, so long as translocation activity is retained. The translocation domain can function as follows.

endosomes having an acidic environment, the peptide is cleaved by the protease furin between Arg279 and Gly280. Then, the disulfide bond is reduced (a mutation at Arg279 inhibits proteolytic cleavage and subsequent translocation to the cytosol, Ogata (1990) J. Biol. Chem. 265:20678–20685). However, a fragment of PE containing the sequence downstream of Arg279 )called "PE37") retains substantial ability to translocate to the cytosol (Siegall (1989) J. Biol Chem. 264:14256–14261). Sequences in domain II beyond amino acid 345 also can be deleted without inhibiting translocation. Furthermore, amino acids at positions 339 and 343 appear to be necessary for translocation (Siegall (1991) Biochemistry 30:7154–7159). Methods for determining the functionality of a translocation domain are well known in the art, as noted above and described.

Domain Ib of PE has no known function. It spans amino acids 365 to 399 of the naturally occurring toxin.

The Psuedomonas exotoxin ADP-ribosylation domain, or domain III, is responsible for cytotoxicity. The naturally expressed PE includes an endoplasmic reticulum retention sequence which may be retained in the toxin polypeptide of the invention. Domain III mediates ADP ribosylation of elongation factor 2 ("EF-2") to inactivate protein synthesis. Domain III of PE spans amino acids 400 to 613. PE is "non-toxic" if it lacks EF-2 ADP ribosylation activity. Genetically modified forms of PE are described in, e.g., Pastan et al., U.S. Pat. No. 5,602,095; Pastan et al., U.S. Pat. No. 5,512,658 and Pastan et al., U.S. Pat. No. 5,458,878. As noted above, *Pseudomonas* exotoxin translocation domain and *Pseudomonas* exotoxin ADP-ribosylation domain (and "substance P peptide) include polypeptides having an activity and a structural characteristic which substantially corresponds to their corresponding polypeptides, including "analogs," "conservative variants," "peptiomimetics" and "mimetics."

An exemplary *Pseudomonas* exotoxin translocation domain comprises an amino acid sequence as set forth in SEQ ID NO:1, which has an amino acid sequence the same as residues 280 to 364 of SEQ ID NO:6 (domain Ib has been deleted, see below) except that an initiating methionine is used as residue in place of the gylcine at residue 280 (in naturally occurring SEQ ID NO:6) (see also Theur (1993) Cancer Res. 53:340–347).

```
SEQ ID NO:1:
Met Trp Glu Gln Leu Glu Gln Cys Gly Tyr Pro Val Gln Arg Leu Val Ala Leu

Tyr Leu Ala Ala Arg Leu Ser Trp Asn Gln Val Asp Gln Val Ile Arg Asn Ala

Leu Ala Ser Pro Gly Ser Gly Gly Asp Leu Gly Glu Ala Ile Arg Glu Gln Pro

Glu Gln Ala Arg Leu Ala Leu Thr Leu Ala Ala Ala Glu Ser Glu Arg Phe Val

Arg Gln Gly Thr Gly Asn Asp Glu Ala Gly Ala Ala Asn
```

After binding to a receptor on the cell surface, the toxin enters the cell by endocytosis through clathrin-coated pits. In the naturally expressed PE, residues 265 and 287 are cysteines that form a disulfide loop. Once internalized into An exemplary *Pseudomonas* exotoxin ADP-ribosylation domain comprises an amino acid sequence as set forth in SEQ IN NO:2, which corresponds to amino acids 400 to 613 of SEQ ID NO:6.

SEQ ID NO:2:
Phe Leu Gly Asp Gly Gly Asp Val Ser Phe Ser Thr Arg Gly Thr Gln Asn Trp Thr Val Glu Arg Leu Leu Gln Ala His Arg Gln Leu Glu Glu Arg Gly Tyr Val Phe Val Gly Tyr His Gly Thr Phe Leu Glu Ala Ala Gln Ser Ile Val Phe Gly Gly Val Arg Ala Arg Ser Gln Asp Leu Asp Ala Ile Trp Arg Gly Phe Tyr Ile Ala Gly Asp Pro Ala Leu Ala Tyr Gly Tyr Ala Gln Asp Gln Glu Pro Asp Ala Arg Gly Arg Ile Arg Asn Gly Ala Leu Leu Arg Val Tyr Val Pro Arg Ser Ser Leu Pro Gly Phe Tyr Arg Thr Ser Leu Thr Leu Ala Ala Pro Glu Ala Ala Gly Glu Val Glu Arg Leu Ile Gly His Pro Leu Pro Leu Arg Leu Asp Ala Ile Thr Gly Pro Glu Glu Glu Gly Gly Arg Leu Glu Thr Ile Leu Gly Trp Pro Leu Ala Glu Arg Thr Val Val Ile Pro Ser Ala Ile Pro Thr Asp Pro Arg Asn Val Gly Gly Asp Leu Asp Pro Ser Ser Ile Pro Asp Lys Glu Gln Ala Ile Ser Ala Leu Pro Asp Tyr Ala Ser Gln Pro Gly Lys Pro Pro Arg Glu Asp Leu Lys The polypeptides of the invention include conservative variants, mimetics and analogs which have modified amino acid sequences such that the change(s) do not substantially alter the variants activity. Thus, a *Pseudomonas* exotoxin translocation domain with conservative variants is within the scope of the invention if it is capable of translocating through an endosomal/microsomal membrane into the cytosol (means for such determinations are well known in the art, see, e.g., Theuer (1994) supra).

A *Pseudomonas* exotoxin ADP-ribosylation domain with conservative variants is within the scope of the invention if, after translocation to the cytosol, can inhibit protein synthesis by ADP-ribosylating elongation factor 2 (means for such determinations are well known in the art, see, e.g. Zdanovsky (1993) supra).

The nucleotide sequence (SEQ ID NO:5) and deduced amino acid sequence (SEQ ID NO:6) of *Pseudomonas areoginosa* exotoxin A are:

```
GCC GAA GAA GCT TTC GAC CTC TGG AAC GAA TGC GCC AAA GCC TGC GTG        48
Ala Glu Glu Ala Phe Asp Leu Trp Asn Glu Cys Ala Lys Ala Cys Val
1               5                   10                  15

CTC GAC CTC AAG GAC GGC GTG CGT TCC AGC CGC ATG AGC GTC GAC CCG        96
Leu Asp Leu Lys Asp Gly Val Arg Ser Ser Arg Met Ser Val Asp Pro
            20                  25

GCC ATC GCC GAC ACC AAC GGC CAG GGC GTG CTG CAC TAC TCC ATG GTC       144
Ala Ile Ala Asp Thr Asn Gly Gln Gly Val Leu His Tyr Ser Met Val
        35                  40                  45

CTG GAG GGC GGC AAC GAC GCG CTC AAG CTG GCC ATC GAC AAC GCC CTC       192
Leu Glu Gly Gly Asn Asp Ala Leu Lys Leu Ala Ile Asp Asn Ala Leu
    50                  55                  60

AGC ATC ACC AGC GAC GGC CTG ACC ATC CGC CTC GAA GGC GGC GTC GAG       240
Ser Ile Thr Ser Asp Gly Leu Thr Ile Arg Leu Glu Gly Gly Val Glu
65                  70                  75                  80

CCG AAC AAG CCG GTG CGC TAC AGC TAC ACG CGC CAG GCG CGC GGC AGT       288
Pro Asn Lys Pro Val Arg Tyr Ser Tyr Thr Arg Gln Ala Arg Gly Ser
                85                  90                  95

TGG TCG CTG AAC TGG CTG GTA CCG ATC GGC CAC GAG AAG CCC TCG AAC       336
Trp Ser Leu Asn Trp Leu Val Pro Ile Gly His Glu Lys Pro Ser Asn
            100                 105                 110

ATC AAG GTG TTC ATC CAC GAA CTG AAC GCC GGC AAC CAG CTC AGC CAC       384
Ile Lys Val Phe Ile His Glu Leu Asn Ala Gly Asn Gln Leu Ser His
        115                 120                 125

ATG TCG CCG ATC TAC ACC ATC GAG ATG GGC GAC GAG TTG CTG GCG AAG       432
Met Ser Pro Ile Tyr Thr Ile Glu Met Gly Asp Glu Leu Leu Ala Lys
    130                 135                 140
```

```
CTG GCG CGC GAT GCC ACC TTC TTC GTC AGG GCG CAC GAG AGC AAC GAG    480
Leu Ala Arg Asp Ala Thr Phe Phe Val Arg Ala His Glu Ser Asn Glu
145                 150                 155                 160

ATG CAG CCG ACG CTC GCC ATC AGC CAT GCC GGG GTC AGC GTG GTC ATG    528
Met Gln Pro Thr Leu Ala Ile Ser His Ala Gly Val Ser Val Val Met
                165                 170                 175

GCC CAG ACC CAG CCG CGC CGG GAA AAG CGC TGG AGC GAA TGG GCC AGC    576
Ala Gln Thr Gln Pro Arg Arg Glu Lys Arg Trp Ser Glu Trp Ala Ser
        180                 185                 190

GGC AAG GTG TTG TGC CTG CTC GAC CCG CTG GAC GGG GTC TAC AAC TAC    624
Gly Lys Val Leu Cys Leu Leu Asp Pro Leu Asp Gly Val Tyr Asn Tyr
            195                 200                 205

CTC GCC CAG CAA CGC TGC AAC CTC GAC GAT ACC TGG GAA GGC AAG ATC    672
Leu Ala Gln Gln Arg Cys Asn Leu Asp Asp Thr Trp Glu Gly Lys Ile
210                 215                 220

TAC CGG GTG CTC GCC GGC AAC CCG GCG AAG CAT GAC CTG GAC ATC AAA    720
Tyr Arg Val Leu Ala Gly Asn Pro Ala Lys His Asp Leu Asp Ile Lys
225                 230                 235                 240

CCC ACG GTC ATC AGT CAT CGC CTG CAC TTT CCC GAG GGC GGC AGC CTG    768
Pro Thr Val Ile Ser His Arg Leu His Phe Pro Glu Gly Gly Ser Leu
                245                 250                 255

GCC GCG CTG ACC GCG CAC CAG GCT TGC CAC CTG CCG CTG GAG ACT TTC    816
Ala Ala Leu Thr Ala His Gln Ala Cys His Leu Pro Leu Glu Thr Phe
        260                 265                 270

ACC CGT CAT CGC CAG CCG CGC GGC TGG GAA CAA CTG GAG CAG TGC GGC    864
Thr Arg His Arg Gln Pro Arg Gly Trp Glu Gln Leu Glu Gln Cys Gly
            275                 280                 285

TAT CCG GTG CAG CGG CTG GTC GCC CTC TAC CTG GCG GCG CGG CTG TCG    912
Tyr Pro Val Gln Arg Leu Val Ala Leu Tyr Leu Ala Ala Arg Leu Ser
290                 295                 300

TGG AAC CAG GTC GAC CAG GTG ATC CGC AAC GCC CTG GCC AGC CCC GGC    960
Trp Asn Gln Val Asp Gln Val Ile Arg Asn Ala Leu Ala Ser Pro Gly
305                 310                 315                 320

AGC GGC GGC GAC CTG GGC GAA GCG ATC CGC GAG CAG CCG GAG CAG GCC    1008
Ser Gly Gly Asp Leu Gly Glu Ala Ile Arg Glu Gln Pro Glu Gln Ala
                325                 330                 335

CGT CTG GCC CTG ACC CTG GCC GCC GCC GAG AGC GAG CGC TTC GTC CGG    1056
Arg Leu Ala Leu Thr Leu Ala Ala Ala Glu Ser Glu Arg Phe Val Arg
        340                 345                 350

CAG GGC ACC GGC AAC GAC GAG GCC GGC GCG GCC AAC GCC GAC GTG GTG    1104
Gln Gly Thr Gly Asn Asp Glu Ala Gly Ala Ala Asn Ala Asp Val Val
            355                 360                 365

AGC CTG ACC TGC CCG GTC GCC GCC GGT GAA TGC GCG GGC CCG GCG GAC    1152
Ser Leu Thr Cys Pro Val Ala Ala Gly Glu Cys Ala Gly Pro Ala Asp
370                 375                 380

AGC GGC GAC GCC CTG CTG GAG CGC AAC TAT CCC ACT GGC GCG GAG TTC    1200
Ser Gly Asp Ala Leu Leu Glu Arg Asn Tyr Pro Thr Gly Ala Glu Phe
385                 390                 395                 400

CTC GGC GAC GGC GGC GAC GTC AGC TTC AGC ACC CGC GGC ACG CAG AAC    1248
Leu Gly Asp Gly Gly Asp Val Ser Phe Ser Thr Arg Gly Thr Gln Asn
                405                 410                 415

TGG ACG GTG GAG CGG CTG CTC CAG GCG CAC CGC CAA CTG GAG GAG CGC    1296
Trp Thr Val Glu Arg Leu Leu Gln Ala His Arg Gln Leu Glu Glu Arg
        420                 425                 430

GGC TAT GTG TTC GTC GGC TAC CAC GGC ACC TTC CTC GAA GCG GCG CAA    1344
Gly Tyr Val Phe Val Gly Tyr His Gly Thr Phe Leu Glu Ala Ala Gln
            435                 440                 445

AGC ATC GTC TTC GGC GGG GTG CGC GCG CGC AGC CAG GAC CTC GAC GCG    1392
Ser Ile Val Phe Gly Gly Val Arg Ala Arg Ser Gln Asp Leu Asp Ala
450                 455                 460
```

-continued

```
ATC TGG CGC GGT TTC TAT ATC GCC GGC GAT CCG GCG CTG GCC TAC GGC            1440
Ile Trp Arg Gly Phe Tyr Ile Ala Gly Asp Pro Ala Leu Ala Tyr Gly
465                 470                 475                 480

TAC GCC CAG GAC CAG GAA CCC GAC GCA CGC GGC CGG ATC CGC AAC GGT            1488
Tyr Ala Gln Asp Gln Glu Pro Asp Ala Arg Gly Arg Ile Arg Asn Gly
                485                 490                 495

GCC CTG CTG CGG GTC TAT GTG CCG CGC TCG AGC CTG CCG GGC TTC TAC            1536
Ala Leu Leu Arg Val Tyr Val Pro Arg Ser Ser Leu Pro Gly Phe Tyr
            500                 505                 510

CGC ACC AGC CTG ACC CTG GCC GCG CCG GAG GCG GCG GGC GAG GTC GAA            1584
Arg Thr Ser Leu Thr Leu Ala Ala Pro Glu Ala Ala Gly Glu Val Glu
            515                 520                 525

CGG CTG ATC GGC CAT CCG CTG CCG CTG CGC CTG GAC GCC ATC ACC GGC            1632
Arg Leu Ile Gly His Pro Leu Pro Leu Arg Leu Asp Ala Ile Thr Gly
    530                 535                 540

CCC GAG GAG GAA GGC GGG CGC CTG GAG ACC ATT CTC GGC TGG CCG CTG            1680
Pro Glu Glu Glu Gly Gly Arg Leu Glu Thr Ile Leu Gly Trp Pro Leu
545                 550                 555                 560

GCC GAG CGC ACC GTG GTG ATT CCC TCG GCG ATC CCC ACC GAC CCG CGC            1728
Ala Glu Arg Thr Val Val Ile Pro Ser Ala Ile Pro Thr Asp Pro Arg
                565                 570                 575

AAC GTC GGC GGC GAC CTC GAC CCG TCC AGC ATC CCC GAC AAG GAA CAG            1776
Asn Val Gly Gly Asp Leu Asp Pro Ser Ser Ile Pro Asp Lys Glu Gln
            580                 585                 590

GCG ATC AGC GCC CTG CCG GAC TAC GCC AGC CAG CCC GGC AAA CCG CCG            1824
Ala Ile Ser Ala Leu Pro Asp Tyr Ala Ser Gln Pro Gly Lys Pro Pro
            595                 600                 605

CGC GAG GAC CTG AAG                                                        1839
Arg Glu Asp Leu Lys
    610
```

Assessing Translocation to the Cytosol

Any functional *Pseudomonas* polypeptide translocation domain can be used in the toxin conjugate of the invention. The functionality of a translocation domain can be tested as a function of the domain's ability to mediate and gain access to the cytosol (because access first requires binding to the cell, these assays are also useful to determine whether the SP domain is functioning, i.e., binding to an NK-1 expressing cell). In one method, access to the cytosol is determined by detecting the physical presence of the toxin conjugate in the cytosol. For example, the toxin conjugate can be labeled with a composition that is detectable after the toxin conjugate gains entry inside a cell. Then, the cytosolic fraction is isolated (the endosomal compartment can also be separately isolated) and the amount of label in the cytosol fraction determined. Detecting label in the cytosol indicates that the translocation domain is functional and that the toxin conjugate has gained access to the cytosol.

Assessing ADP Ribosylation Activity

Any functional *Pseudomonas* polypeptide translocation domain can be used in the toxin conjuate of the invention. The functionality of a domain III having ADP ribosylation activity can also be tested in a variety of ways. For example, cells can be seeded in tissue culture plates and expoed to the toxin conjuate. ADP ribosylation activity is determined as a function of inhibition of protein synthesis by, e.g., monitoring the incorporation of $^3$H-leucine.

Recombinant Expression of *Pseudomonas* Polypeptide Domains

The functional *Pseudomonas* polypeptide translocation and ADP ribosylation domains can be expressed in any in vitro or in vivo recombinant system. In one exemplary system, *Pseudomonas* polypeptide translocation and ADP ribosylation domains are designed as a single recombinant molecule based on the naturally expressed toxin (SEQ ID NO:6). In one exemplary design the recombinant molecules uses an initiating methionine in place of glycine at residue 280 (of SEQ ID NO:6), retains the cysteine of residue position 287, and eliminates the disulfide bond at residues 374 to 379; the resulting polypeptide is SEQ ID NO:1.

In one exemplary recombinant system, SEQ ID NO:1 (or equivalent thereof) is expressed into the periplasm of *E. coli* (using standard techniques, see, e.g., Sambrook). There, a large proportion of the toxin dimerizes by forming a disulfide bond (linking cysteins 287). Prior to conjugation, PE recombinant polypeptide preparations are treated with 2-mercaptoethanol and separated on a size exclusion chromatography column (using standard techniques). Any remaining dimers elute first, followed by monomer fractions, which are appropriately collected for further conjugation to SP-thionitrobenzoic acid derivatized peptide, as described below.

Substance P and the NK-1 Receptor

An important pain-mediating peptide is the eleven amino acid long Substance P ("SP"). SP plays a central role in the transduction of second messenger signals from primary afferent nociceptive terminals to second-order neurons in the spinal cord (see, e.g., Lembeck (1981) supra). SP transduces a pain signal by interacting primarily with neurokini-1 ("NK1") receptor-bearing cells in the brain and spinal chord (see, e.g., Abbadie (1996) supra; Seelig (1996) Biochemistry 35:4365–4374). One of the most studied SP circuits is the connection between primary afferent nociceptive dorsal root ganglion neurons and second order neurons in the spinal cord. This SP mediated signal is known to mediate pain signals. These second order neurons are essential links in the classical trisynaptic pathway of pain transmission from the periphery to the spinal cord to the thalamus to the somatosensory are of the cortex.

An SP peptide or variant thereof is within the scope of the invention if it is capable of binding to an NK-1 receptor expressed on a eukaryotic cell, such as human cell (binding protocols for such determinations are well known in the art, see, e.g., Ciucci (1998) Br. J. Pharmacol. 125:393–401; Maguire (1998) Brain Res. 786:263–266; Quartara (1998) supra) and discussion below. SP peptide used in the toxin conjugates of the invention are further modified by the addition of a sulfhydryl group, e.g., a cysteine residue or equivalent, to the amino terminus of the peptide (for disulfide linked conjugation, as discussed below). Additional of a sulfhydryl group to the amino terminus is important because the carboxy-terminus of the SP peptide must be amidated for the peptide to bind to the NK-1 receptor. SP peptides used in the invention can be amidated on their carboxy termini by any means, e.g., by amidation of peptides which have been made synthetically or by the method set forth in Fisher (1996) supra (page 7342).

The invention provides a pharmaceutical composition and a method for the ablation of NK1 receptor expressing cells. Thus, the cell toxins of the invention can bind to (and kill) any NK1 receptor expressing cell. While pain mediating cells and neurons are the predominant cells expressing NK-1 receptors (e.g., spinal cord dorsal horn neurons, see, e.g., Basbaum (1999) supra), brain cells, see, e.g., Saria (1999) supra; neostriatum cells through the axon collaterals of spiny projection neurons, see, e.g., Galarrga (1999) supra), a variety of other normal or abnormal (e.g., tumor) cells also express NK-1 receptor and thus can be killed practicing this invention. Thus, the cell toxins and methods of the invention can be used to treat a variety of different conditions or to modify a variety of different physiologic mechanisms. For example, spinal NK1 receptors modulate autonomic reflexes, including the micturition reflex. In the peripheral nervous system, NK1 receptors are widely expressed in the respiratory, genitourinary and gastrointestinal tracts and are also expressed by several types of inflammatory and immune cells. In the cardiovascular system, NK1 receptors mediate endothelium-dependent vasodilation and plasma protien extravasation. At respiratory level, NK1 receptors mediate neurogenic inflammation which is especially evident upon exposure of the airways to irritants. In the carotid body, NK1 receptors mediate the ventilatory response to hypoxia. In the gastrointestinal system, NK1 receptors mediate smooth muscle contraction, regulate water and ion secretion and mediate neuro-neuronal communication. In the genitourinary tract, NK1 receptors are widely distributed in the renal pelvis, ureter, urinary bladder and urethra and mediate smooth muscle contraction and inflammation in response to noxious stimuli. NK1 receptors antagonists, including toxins that can ablate NK-1 receptor expression cells, may have several therapeutic applications at central and peripheral level. In the central nervous system, NK1 receptor ablation toxins could be used to produce analgesia, as antiemetics and for treatment of certain forms of urinary incontinence due to detrusor hyperreflexia. In the peripheral nervous system, toxins of the invention could be used in severl inflammatory diseases including arthritis, inflammatory bowel diseases and cystitis (Quartara (1998) supra).

Further uses of the toxins and methods of the invention are suggested by, e.g., Al, et al., who show that SP and its receptor are expressed in human peripheral blood-isolated lymphocytes (Lai (1998) J. Neuroimmunol. 86:80–86). Using cultured rabbit osteoclasts, Mori et al. found that SP possibly stimulates the bone remodeling by osteoclasts (Mori (1999) Biochem. Biophys. Res. Commun. 262:418–422). SP present in bronchial nerve fibers can induce relaxation of rat bronchial smooth muscle (Bodelsson (1999) Respiration 66:355–359). SP has aniolytic-like effects when administered into the nucleus basalis of the rat ventral pallidum (Nikolaus (1999) Neuroreport (10:2293–2296). Baraniuk, et al. showed that a nociceptive nerve efferent axon response may lead to glandular exocytosis through actions on submucosal gland NK-1 receptors (Baraniuk (1999) Am. J. Respir. Crit. Care Med. 160:655–662). Mauback, et al. showed that a SP receptor antagonist had antidepressant efficacy (Maubach (1999) Curr. Opin. Chem. Biol. 3:481–488). Santoni, et al. speculates that SP plays a major role in the regulation of the interaction between immuned and nervous systems. Santoni (1999) J. Neuroimmunol. 93:15–25).

The conjugates may also be used in the treatment of neurological dysfunctions of the basal ganglia by targeting cholinergic interneurons that express SP (e.g. Parkinsons Disease, see, e.g., Kaneko Science 289:633–637, 2000). In such a use, the compostion is typically administered directly to the brain.

Disulfide Linked Cell Toxin Conjugates

The invention provides disulfide linked cell toxin conjugates comprising a modified SP peptide and a modified PE translocation domain linked to a PE ADP-ribosylation domain. chemical conjuation is advantageous over synthesis by, e.g., entirely recombinant techniques, because a better defined homogenous product is obtained (recombinant expression in vivo, e.g., mammalian cells or bacteria, in contrast, commonly results in mixed products due to post-translational modification, degradation, and the like). In the present invention, conjugates are made by "disulfide exchange." To ensure that the ratio of SP to PE in each conjugate molecule is 1:1, the SP peptide and the *Pseudomonas* exotoxin component of the toxin conjugate each have only one reactive sulfhydryl group. The sulfhydryl group for disulfide exchange can be in the form of a cysteine (or equivalent, see above) residue.

To make the conjugate, the SP-cysteeine (or equivalent) (e.g., SEQ ID NO:4), generated by solid phase synthesis, initially purified, and amidated. It next reacted with dithio-bis(2-nitro)-benzoic acid (DTNB). This reaction yields a thionitrobenzoic acid derivatized SP peptide ("SP-TNB") and a thionitro benzoate group.

In one exemplary protocol, SP-TNB is added to the pseudomonas exotoxin component (having only one reactive sulfhydryl group) in a 8:1 molar ratio for an overnight incubation at 4C. Progress of the reaction is monitored, e.g., by measuring absorbance at OD 412 nm. SP-TNB can be purified, e.g., by HPLC. The SP-PE pharmaceuticals of the invention have less than 2% thionitro benzoate groups.

SP-TNB is dissolved in 20% DMSO (e.g., 2 mg SP-TNB in 20 microliters DMSO). Then 1.0 milliliter of 0.2 molar Na-phosphate is added (pH 7.0). The conjugation mixture is applied to gel filtration column (e.g., G-25) to remove unreacted SP-TNB and eluted. The mixture was fixture purified by HPLC gel filtration to remove unreacted PE polypeptide. Fractions are collected and analyzed by Western blot to confirm the presence of *Pseudomonas* exotoxin domain (by reaction with monoclonal anti-PE antibody) and monoclonal anti-SP antibody (directed to the amidated carboxy terminus of the SP). The presence of a disulfide linkage is confirmed by reduction (e.g., with 2-ME or dithiothreito) followed by gel electrophoresis (e.g., SDS-PAGE) and Western blot analysis with the above referenced monoclonal antibodies. Fractions containing one to one (1:1) PE to SP molar relationship conjugates are retained and stored, e.g., at $-80°$ C.

Formulation and Administration Pharmaceuticals

The cell toxin conjugates of the invention are formulated as pharmaceuticals to be used in the methods of the invention to treat pain, particularly chronic pain. These pharmaceuticals can be administered by any means in any appropriate formulation. Routine means to determine drug regimens and formulatins to practice the methods of the invention are well described in the patent and scientific literature, and some illustrative examples are set forth below. For example, details on techniques for formulation and administration are well described in the scientific and patent literature, see, e.g., the latest edition of Remington's Pharmaceutical Sciences, Maack Publishing Co, Easton, Pa.

The pharmaceutical composition of the invention is administered such that the cell toxin conjugate is anatomically approximate to an NK-1 recetor bearing cell, e.g., a nerve, including, e.g., epineurium or perineurium, tissue surrounding nerve ganglia, nerve sheathes, nerve linings, or meninges, e.g., the pia mater, or arachnoid or dura membranes. The pharmaceutical composition can be administered into the subarachnoid space. The pharmaceutical composition can be administered in or approximate to joints for, e.g., the treatment of chronic pain associated with arthritis.

The pharmaceutical composition can be administered intrathecally (i.e., into the CSF in the subarachnoid space), where the concentration of cell toxin conjugate in the pharmaceutically acceptable excipient can be betwwen about is 0.5 to about 50 mL of a formulation at dosages equivalent to about 0.2 to about 0.6 mg/kg, or, about 0.1 to about 1.0 mg/kg, or, about 0.2 to $10^3$ nanograms per microliter, depending on a variety of conditions, as described below. The delivery can be through implanted or external intrathecal or epidural pumps, see, e.g., Hassenbusch (1999) Oncology 13)5 Suppl 2):63-7.

Aqueous suspensions of the invention can also include any excipients or admixture suitable for the manufacture of aqueous suspensions. The aqueous suspension can also contain one or more preservatives, such as ethyl or n-propyl p-hydroxybenzoate. The aqueous suspeonsion can be adjusted for osmolarity. The aqueous solution can be adjusted to promote the stability of the vector for lyophilization. For example, a cryoprotectant solution that can significantly maintain stability after freeze-thaw cycles.

The pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM–50 mM histidine, 0.1%–2% sucrose, 2%–7% mannitol at a pH range of 4.5 to 5.5, that is combined with the appropriate aqueous buffer prior to use.

After a pharmaceutical comprising a cell toxin conjugate of the invention has been formulated in an acceptable carrier/excipient it can be placed in an appropriate container, e.g., as a kit, and labeled for treatment of the indicated condition. for administration of the pharmaceutical compositions of the invention, such labeling would include, e.g., instructions concerning the amount, frequency and method of administration. These instructions can also be part of a kit.

The cell toxin conjugates of the invention can also be formulated as cationic lipid-nucleic acid compositions for administration in a variety of ways. Details on techniques for formulation and administration are well described in the scientific and patent literature, see, e.g., the latest edition of "Remington's Pharmaceutical Sciences" (Maack Publishing Co, Easton Pa.). See also, Lasic and Templeton (1996) Adv. Drug Deliv. Rev. 20:221–266 and references cited therein. The ratios of each component in the cationic lipid-nucleic acid complexes, final concentrations, buffer solutions, and the like can be readily optimized by the skilled artisan, taking into consideration the mode of delivery (i.e., intrathecal, epidural, intra-articular, direct injection into brain or spinal cord parenchyma), the anatomical site of delivery, any existent conditons or diseases, the condition and age of the patient, and the like. Methods of producing cationic liposomes are known in the art (see e.g., Liposome Technology (CFC Press, N.Y. 1984); Liposomes, Ortro (Marcel Schler, 1987).

Determining Dosing Regiments

The pharmaceutical formulations of the invention can be administered in a variety of unit dosage forms, depending upon the particular condition or disease, the degree of chronic pain, the general medical condition of each patient, the method of administration, and the like. Details on dosages are well described in the scientific and patent literature, see, e.g., the lastest edition of Remington's Pharmaceutical Sciences, Maack Publishing Co, Easton Pa.

The exact amount and concentration of cell toxin conjugate and the amount of formulation in a given dose, or the "therapeutically effective dose" is determined by the clinician, as discussed above. The dosage schedule, i.e., the "dosing regimen," will depend upon a variety of factors, including, e.g., the amount of chronic pain present, the duration of the pain, the stage and severity of the disease or condition associated with the chronic pain (if any), and the general state of the patient's health, physical status, age and the like. The state of the art allows the clinician to determine the dosage regimen for each individual patient and, if appropriate, concurrent disease or condition travel, see, e.g. Selvaggi (1993) J. Immunother, 13:201–207.

One typical dosage is between about 0.5 to about 50 mL of a formulation at dosages equivalent to about 0.2 to about 0.6 mg/kg daily (however, the dosage can be adjusted, as described below, from about 0.01 to about 2.0 mg/kg). Dosage levels and frequency of administration (daily for several days, every other day, etc.) are based on objective and subjective criteria, as discussed herein. Any dosage can be used as required and tolerated by the patient. Furthermore, the exact concentration of toxin conjugate, the amount of formulation, and the frequency of administration can be adjusted depending on the levels of SP-PE measured in the CSF after an initial administration. Means to sample CSF or other fluid or tissue samples and detect and quantitate levels of SP-PE are well known in the art (see Example 1, below).

Routes of Administration

The pharmaceutical compositions of the invention can be administered by any means know in the art to any anatomical space, e.g., intrathecally, subdurally, direct injection in brain or spinal cord parenchyma. If treating a cancer that expresses a receptor that binds to SP (e.g. NK-1 receptor), the pharmaceutical can also be administered, e.g., intravenously or directly into the tumor. The pharmaceutical composition of the invention can be administered to any cell which expresses NK-1 receptors, including, but not limited to epineurium cells, perineurium cells, nerve ganglia, nerve sheathes, nerve linings, meninges, pia mater cells, arachnoid membrane cells, dura membrane cells, cells lining a joint or brain or spinal cord parenchymal cells. For example, the pharmaceutical composition can be administered intrathecally or epidurally in a pharmaceutically acceptable excipient. Means to administer solutions into all of these anatomical compartments are well known in the art, see, e.g., the subarachnoid space, i.e., intrathecally, into the CSF, see, e.g., Oyama, T., U.S. Pat. No. 4,313,937; discussing intratecal pumps, see, e.g., Nance (1999) Phys. Med. Rehabil. Clin. N. Am. 10:385–401; Anderson (1999) Neurosurgery 44:289–300.

The cell toxin of the invention can be administered by single or multiple or continuous infusion (e.g., by pumps, internal or external) into the intrathecal or epidural space, or directly into brain or spinal cord parenchyma, depending on the dosage and frequency as required and tolerated by the patient.

Kits

The invention provides a kit for the treatment of chronic pain in a human which includes a pharmaceutical composition of the invention. The kit can contain instructional material teaching preferred indications, dosages and schedules of administration, and the like.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

The following example is offered to illustrate, but not to limit the claimed invention.

Example 1

Substance P-*Pseudomonas* Exotoxin Disulfide Linked Conjugate Selectively and Potently Kills Neurokinin-1 Receptor Expressing Cells The followng example details a study which demonsrates that compositions and methods of the invetnion can be practiced to ablate NK-1 receptor expressing cells. Specifically, this study demonstrates that CHO cells stably transfected with and expressing NK-1 receptors, but not NK-2 or NK-3 receptors, can be killed by the SP-PE cell toxin conjugate of the invention.

A disulfide linked SP-PE cell toxin was made as described above. Specifically, an synthetic SP peptide (SEQ ID NO:4) was carboxy-terminal amidated prior to conjuation using standard techniques.

The carboxy-terminal amidated, N-terminal thionitrobenzoic acid derivatized SP peptide was reacted with a recombinant PE polypeptide having a N-terminal domain with a sequence as set forth in SEQ ID NO:1 and a carboxy-terminal domain (the translocation domain) with a sequence as set forth in SEQ ID NO:2 ) the ADP-ribosylation domain). The cell toxin conjugate was purified and analyzed for the presence of disulfide linkage, SP peptide and PE domains as describe above. The preparation was substantially pure of free thionitrobenzoate groups.

CHO cells were stably transfected with either NK-1, NK-2 or NK-3 receptor encoding nucleic acid sequences (see, e.g., Maggi (1997) Trends Pharmacol. Sci. 18:351–355; Tian (1996) J. Neurochem. 67:1191–1199) using conventional techniques. Cell surface expression of each respective receptor was confirmed by reaction with receptor specific antibodies (see, e.g., Dery (1997) J. Neuroimmunol. 76:1–9); Arkinstall (1995) FEBS Letters 375:183–187.

NK-1, NK-2, or NK-3 receptor-expressing CHO transformant cell cultures were grown to 90% confluence. The cultures were exposed to the SP-PE cell toxin for various times, including 1.5 minutes, 3 hours, and 24 hours. After exposure, cells were washed and allowed to proliferate for a further 24 or 48 hours. At these times media and an non-adherent cells (i.e., dead cells) were removed and the cultures fixed and stained with toluidine/methylene blue in ethanol. These stained cultures were photographed and the images on the slides were digitized by scanning with a digital camera. The average number of live/dead cells per plate was calculated by using the "analyze" and "histogram" functions in ADOBE™ photoshop program using standard techniques.

The SP-PE toxin was very specific for NK-1 receptor-expressing cells, which were killed with an IC50 of 2 ng/ml ($5 \times 10^{-11}$ M). No killing was seen when NK-1 receptor-expressing cells were incubated with unconjugated PE domains. No killing was seen when NK-2 or NK-3 receptor-expressing cells were exposed to SP-PE toxin.

Toxicity to NK-1 receptor expressing cells were blocked by the addition of excess free SP or by treating the toxin conjugate with an anti-SP antibody. Cytotoxicity occurred with exposure times to toxin as short a two minutes (lethality assessed at 24 hours after exposure).

The specificity for SP-PE toxin for NK-1 receptor-expressing cells was confirmed by incubating the panel of stably transfected cells with tritiated lecuine ($^3$H-leucine) and SP-PE toxin (made as described in Example 1). Viable cells incorporate the amino acid leucine to polypeptides. Dead or dying cells do not synthesize polypeptide and do not incorporate the $^3$H-leucine. FIG. 1 shows a schematic summary of data of experiments testing the ability of the SP-PE conjugate toxin of the invention to kill CHO cells stably transfected with and expressing NK-1 receptors (FIG. 1A), NK-2 receptors (FIG. 1B), and NK-3 receptors (FIG. 1C).

The SP-PE toxin only comprised the viability of NK-1 receptor-expressing cells. The viability of NK-1 and NK-3 receptor expressing cells was the same as the (negative) control. As a (negative) control, in place of SP-PE toxing, the cells were exposed to the PE domain alone (lacking the receptor ligand SP) (designated "PE35" in FIG. 1). PE domain alone did not comprise the viability of any of the transfected cells.

These data demonstrate that the SP-PE toxin conjugates of the invention specifically ablate NK-1 receptor expressing cells.

Example 2

SP-*Pseudomonas* Exotoxin Disulfide Linked Conjugate Kills NK-1-Expressing Cells in Rat Spinal Column Dorsal Horn Cells In Vivo The following example details a study which demonstrates that compositions and methods of the invention can be practiced to ablate NK-1 receptor expressing cells in the dorsal horn of the spinal column in vivo. Specifically, this art-recognized animal model for pain therapy demonstrates that the SP-PE toxin of the invention administered in vivo via intrathecal injection selectively and potently killed dorsal horn NK-1 receptor expressing cells. The toxin conjugate of the invention was extremely effective deleting NK-1 receptor expressing cells from the dorsal horn of the spinal cord and NK-1 receptor expressing cells from the striatum.

Male Sprague-Dawley rats were used in all experiments. All procedures and experimental protocols were approved by an NIH Animal Care and Use Committee and are in accordance with the guidelines of the International Association for the Study of Pain (Zimmermann (1983) Pain 16:109–110). Animals were anesthetized and the SP-PE toxin of the invention (as described in Example 1, above) administered by intrathecal infusion as described by Benoliel (1999) Pain 79:243–253, at a dose of 20 µl containing a concentration of 25 nanograms per µl Tissue preparation and immunocytochemistry were performed as by Benoliel (1999) supra. Tissue sections were harvested eight days after intrathecal treatment with SP-PE toxin (or saline as a negative control). Dorsal horn tissue sections of the spinal cord were stained with antibodies for NK-1 receptor. Sections from animals treated with SP-PE toxin clearly showed significant ablation of SP receptor-expressing cells (loss of anti-NK-1 receptor antibody reactivity) in the dorsal horn of the rat spinal column. Animals treated with saline only showed normal SP receptor-expressing cell staining pattern, i.e., no ablation. The saline control showed strong staining for an antibody reactive NK-1 receptor.

These data demonstrate that the SP-PE toxins of the invention ablate NK-1 receptor expressing cells in the dorsal horn of the spinal column in vivo.

Example 3

SP-*Pseudomonas* Exotoxin Disulfide Linked Conjugate Administered In Vivo Decreased Pain Sensation in a Heat Hyperalgesia Test The following example details a study with an art-recognized animal (rat) model for investigating treatments for pain which shows that the SP-PE compositions of the invention can be used and methods of the invention can be practiced to treat pain.

All animal procedures and intrathecal toxin administrations were as described above (Example 2), as in Benoliel (1999) supra. The SP-PE toxin used was prepared as described in Example 1, above. Heat sensitivity was assayed with a withdrawal latency test as described by Iadarola (1988) Brain Res. 455:205–212, see also Benoliel (1999) supra. Sensitivity to nociceptive thermal stimulation was tested in unrestrained rats with a radiant heat stimulus as described. Briefly, the rat is placed on an elevated glass plate, with a clear plastic cage inverted over the animal. After 5 min habituation to the enclosure, a projector lamp in a conical housing is positioned under the fore or hind paws or tail. The light emerges from an opening in the conical housing light. The latency is recorded automatically when paw or tail movement interrupts the readings of a photocell in the lamp housing. Four rats were tested with toxin and four rats were controls. Assays were conducted 20 days after toxin treatment.

Figure 2:
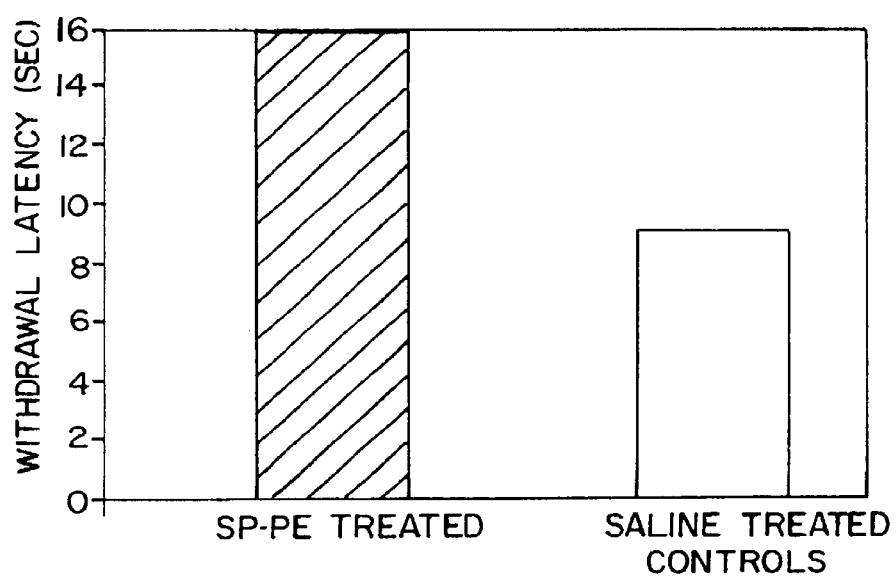
FIG. 2 shows a schematic summary of data of experiments testing the ability of the SP-PE conjugate toxin of the invention to treat pain (as determined by a thermal sensitivity test) in an art accepted (rat) animal model for pain control, as explained in detail in Example 3, below.

FIG. 2 shows a schematic summary of data of experiments testing the ability of the SP-PE conjugate toxin of the invention to treat pain. Administration of SP-PE toxin significantly increased paw withdrawal latency as compared to control (saline only administered). The "normal" or saline control latency was 8 seconds while the "pain desensitized" toxin treated animal had a withdrawal latency of between 14 and 16 seconds. Similar effects are also observed at 8 days following SP-PE administration.

To further evaluate long-term effects and selectivity following SP-PE treatment, control and treated animals were analyzed for withdrawal latency. heat withdrawal latency was tested as decribed in Example 2.

Figure 3:
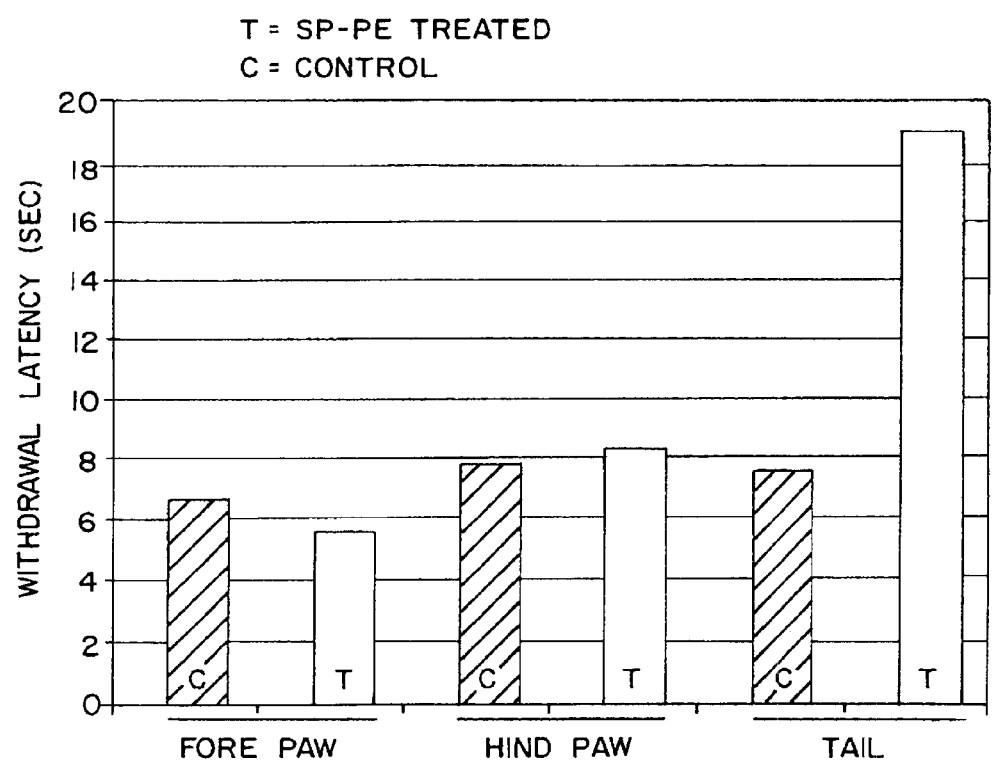
FIG. 3 shows a schematic summary of data of experiments testing the segmental selectivity of SP-PE applied at sacral spinal cord.

The ability of SP-PE to selectively block thermal heat pain in rats at a target region was tested 46 days after intrathecal injection of about 15 picomoles of SP-PE (FIG. 3), which was infused slowly at a rate of about 1 µl per minute (dose of 20 µl containing a concentration of 25 nanograms per µl). In this study, the conjugate was administerd to the region of the cord that affects pain perception in the tail. The results show segmental selectivity of SP-PE applied at sacral spinal cord and demonstrate that the effect of SP-PE treatment can be localized to control the site of action, even though the injection is made into a fluid-filled space.

To demonstrate that administration of SP-PE to rats attenuates a symptom of chronic pain, hyperalgesia, a rat thermal hyperalgesia model was used. This method measures cutaneous hyperalgesia to thermal stimulation in unrestrained animals, and was performed essentially as described by Hargreaves (1988) Pain 32:77–88. Briefly, after administration of expression vector, baseline thermal hyperalgesia is assessed by paw withdrawal latency to thermal stimulus. Inflammation is then induced with unilateral injection of 6 mg carrageenan (type IV Sigma C-3889) in volum of 0.15 mL PBS into a hindpaw of a 200–300 g male rat. Paw withdrawal latency to thermal stimulus is again measured on both the inflamed and uninflamed paws.

Figure 4:
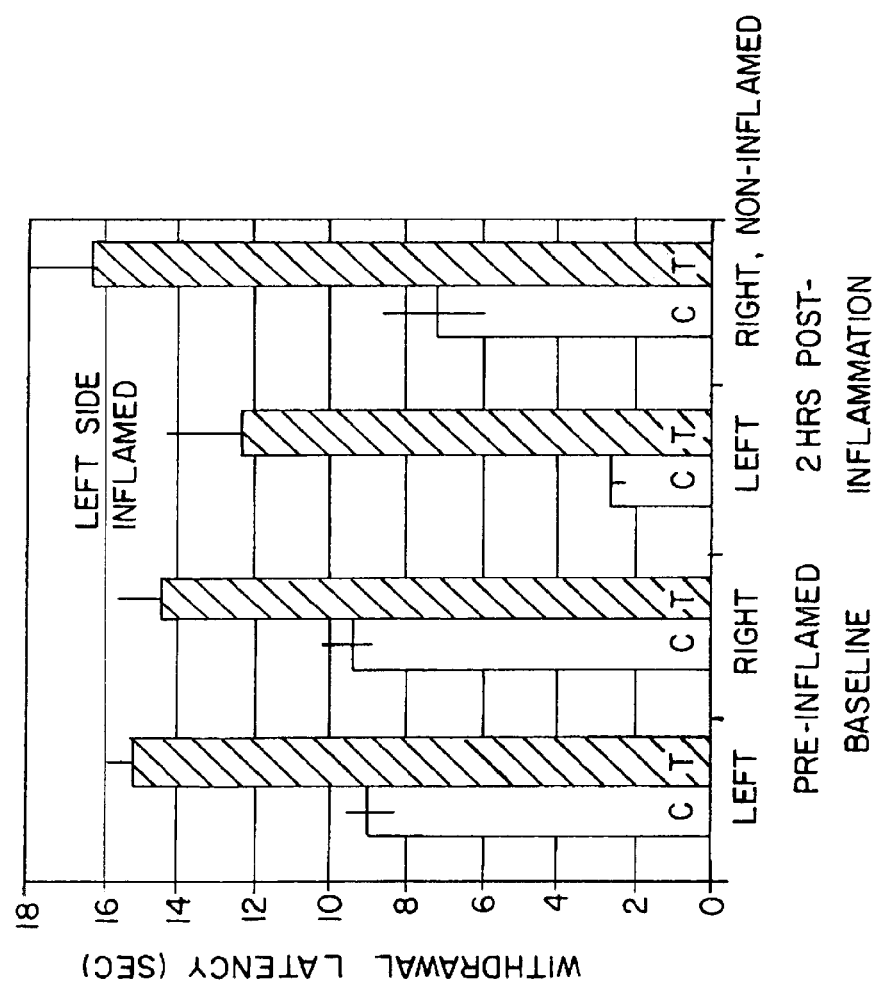
FIG. 4 shows a schematic summary of data of experiments testing the thermal sensitivity in rats at 46 days following intrathecal injection of SP-PE conjugate. The ability of the SP-PE conjugate toxin to treat pain effects in an inflammation model of chronic pain was also tested.

The ability of SP-PE to block acute thermal pain in the foot and to block thermal hyperalgesia in the carrageenan model of hind paw inflammation was tested at 46 days following treatment (FIG. 4). The data obtained from the animals before induction of inflammatin, (the pre-inflamed data) show that 46 days after intrathecal injection of 15 picomoles SP-PE, the treated animals showed an increased withdrawal latency. When tested in the inflammation model system, the treated animals also showed blocking of thermal hyperlgesia, which incates that the SP-PE will also be useful in chronic pain syndromes.

Treatment with SP-PE also blocks mechanical pain, i.e., a mild pinch with a toothed forceps. This effect occurs in a segmental fashion. Thus, if the infusion occurs around the hindpaw region of the spinal cord, the loss of pinch sensitivity is seen in the tail, hind paws, and part of the lower trunk, but not in the upper half of the body.

This art-recognized animal (rat) model for investigating treatments for pain clearly demonstrate that the SP-PE toxin conjugates of the invention are effective in the treatment of pain in vivo.

Example 4

Long Term Effects On Other Neurotransmitter Systems Following SP-PE Treatment

This example shows that other neurotransmitter systems do not undergo long term compensatory rearrangements following treatment with SP-PE.

Compensatory rearrangements of the nervous system might occur after removal of a cell population, which, in turn could alter the therapeutic effects of administration of SP-PE. To evaluate the effects of SP-PE treatment on other neurotransmitter systems, immunocytochemistry for calcitonin gene-related peptide (CGRP) and tyrosine hydroxylase (TH) was performed on dorsal horn tissue samples obtained from control and SP-PE treated animals at 20 days post treatment. Tissue samples were prepared as in Example 2 and sections were stained with antibodies specific for CGRP or TH.

The distribution of CGRP, which is produced by primary afferent neurons, was analyzed 20 days following administeration of 15 picomoles SP-PE. The results showed that the distribution and amount of CGRP observed in tissue samples in the treated animals appeared to be equivalent to that of the control.

Tyosine hydroxylase is involved in the production of the biogenic amines, dopamine, norepinephrine (the transmitter in sympathetic nervous system fibers), and epinephrine. These neurotransmitters have been implicated in rearrangements in the dorsal root ganglion upon nerve injury. The result of the immunocytochemistry analysis at 20 days post treatment showed no consistent effects on TH innervation in treated animals, which is likely due to the fact that only a small population of cells is being removed from the dorsal spinal cord.

These experiments demonstrate that administration of SP-PE does not result in compensatory rearrangement. The magnitude of the decrease in sensitivity to pain in SP-PE treated animals was also equivalent at 70 days after administration of the conjugate to that observed at 20–46 days post-treatment. Further, animals at over 70 days post-treatment exhibited normal locomotion and there was no evidence of autotomy.

Example 5

Intrastriatal Administration of SP-PE

The following example shows that intrastriatal adminstration of SP-PE results in deletion of NK-1 expressing striatal neurons.

Rats administered SP-PE instrastriatally received a atotal dose of 25 ng of the conjugate. Animals were anesthetized and a one µl injection of conjugate was made over about 1 minute into the striatum. The rats were then assessed for apomorphine-induced turning behavior and neuronal toxicity.

A unilateral intrastriatal injection of SP-PE did not produce an appreciable alteration in the rats locomotor activity, posture or gait. However, when challenged with a systemically administered apomorphine, the rats displayed a strong contralateral turning behavior. Apomorphine also produce hyper-locomotion.

Immunocytochemical analysis also showed that the same dose that produced the contralateral turning behavior also produce a marked decrease in NK1 immunoreactive neurons in the rat striatum. The baseline NK1 immunoreactivity was most dense in the dorsal and lateral straitum and was associated with the dendrites of the neurons, although in the ventral striatum and olfactory tubercle, neuronal cell bodies were clearly observed. Previous research has shown that the NK1 positive striatal neurons are the medium spiny cholinergic interneurons. Microinjection of 25 ng of SP-PE (~0.7 picomoles) produced a macroscopically noticeable, unilateral zone of NK1 receptor loss in striatum, in comparison to the contralateral side of the same animal. The neuropil on the non-injected side contained a dense amount of NK1-immunopositive dendrites and cell bodies. These were eliminated from the injected zone on the other side.

The direct intrastriatal injections also provided an opportunity to assess potential toxic effects on non-receptor expressing cells exposed directly to the SP-PE conjugate. The integrity of other neural elements was assessed in two ways. First, the NK1 stained sections were immunocytochemically counter-stained for neurofilament protein, which localizes to the cortico-spinal fiber bundles. The bundles were are not affected by SP-PE even though they are in the center of the zone of medium spiny interneuron denervation. Second, standard histological stains of paraffin embedded thin sections were used to assess pathological changes. The Sections that included the cannula tract were stained with hematoxylin-eosin or luxol-fast blue. If a large amount of non-specific cell death had occurred a widespread loss of neuronal perikarya and a large microglial inflitration surrounding the tip of the cannula could be expected. Neither effect was observed, the appearance of the injected srtiatum was indistinguishable from either surrounding tissue or the contralateral side in which the NK1 receptor bearing cells were unaffected.

Thus, instrastriatal administration of SP-PE produced behavioral effects (contraversive turning with a apomorphine challenge, 3 mg/kg intraperitoneal injection) and selective loss of SPR expressing cholinergic interneurons with no concurrent loss of Mu-opioid receptors.

Example 6

SP-*Pseudomonas* Exotoxin Disulfide Linked Conjugate Administered To Patients with Chronic Pain The following example details the treatment of chronic pain in patients using the SP-PE compositions, e.g., the pharmaceuticals, of the inventions.

As substance P (SP_ peptide is a known mediator of chronic pain (as a ligand for the NK-1 recptor), the SP-PE pharmaceuticals of the invention can be efficaciously administered to virtually any patient having chronic pain. Means to diagnose and assess chronic pain is discussed in detail, above. As noted above, while chronic pain is diagnosed and treatments are assessed using both objection and subjective criteria, a diagnosis of a particular pathologic process (which is usually also chronic) known to produce or be associated with chronic pain is helpful to the clinician in determining when the administer the pharmaceutical compositions of the invention. Such conditions are well characterized and include, e.g., chronic pain syndrome, arthralgia, osteoarthritis and rheumatoid arthritis, causalgia, hyperpathia, neuralgia, neuritis, radiculagia, fibromyalgia, orofacial pain and temporomandibular disorders, reflex sympathetic dystrophy, chronic back pain, certain cancers, and the like.

In one exemplary protocol, patients diagnosed with chronic pain are treated with an SP-PE pharmaceutical compositions suitable for intrathecal administation. While the dosage schedule, i.e., the "dosing regimen," will depend upon a variety of factors, including, e.g., the amount of chronic pain present, the duration of the pain, the stage and severity of the disease or condition associated with the chronic pain (if any), and the general state of the patient's health, physical status, age and the like, one typical dosage is between about 0.5 to about 50 mL of a formulation at dosages equivalent to about 0.2 to about 0.6 mg/kg daily for five days. This is administered by an internal or external intrathecal infusion pump. These pumps, while typically used for administration of opioids, can be used to administer the pharmaceuticals of the present invention, see, e.g., Likar (1999) Arzneimittelforschung 49:489–493; Valentino (1998) J. Neurosci. Nurs. 30:233–239, 243-234.

Dosage levels and frequency of administration are continuously adjusted based on objective and subjective criteria, as discussed herein. Any dosage can be used as required and tolerated by the patient. Furthermore, the exact concentration of toxin conjugate, the amount of formulation, and the frequency of administration can be adjusted depending on the levels of SP-PE measured in the CSF after an initial administration. Means to sample CSF or other fluid or tissue samples and detect and quantitate levels of SP-PE are discussed above.

What is claimed is:

1. A method of making a cell toxin comprisng
reacting a polypeptide comprising a *Pseudomonas* exotoxin translocation domain linked to a *Pseudomonas* exotoxin ADP-ribosylatin domain, wherein the *Pseudomonas* exotoxin translocation domain comprises at least one reactive sulfhydryl group, with a substance P peptide comprising one additional cysteine residue at its amino terminal end, wherein the cysteine sulfhydryl group is disulfide linked to a di-thiobis (2-nitro)-benzoic acid group, such that after the reaction a disulfide bond is formed between the exotoxin polypeptide and the substance P and a thionitrobenzoate group is released, and
purifying the substance P-*Pseudomonas* exotoxin disulfide linked conjugate from the released thionitrobenzoate group such that the purified conjugate is substantially free of thionitrobenzoate groups.

2. The method of claim 1, wherein the *Pseudomonas* exotoxin translocation domain sulfhydryl group located within ten amino acid residues of the translocation domain amino terminus.

3. The method of claim 1, wherein the *Pseudomonas* exotoxin translocation domain sulfhydryl group located at the translocation domain amino terminus.

4. The method of claim 1, wherein the *Pseudomonas* exotoxin translocation domain sulfhydryl group is a cysteine residue.

5. The method of claim 1, wherein the *Pseudomonas* exotoxin translocation domain is covalently linked to the *Pseudomonas* exotoxin ADP-ribosylation domain.

6. The method of claim 5, wherein the covalent linkage between the Pseudomonas exotoxin translocation domain and the *Pseudomonas* exotin ADP-ribosylation domain is a peptide bond.

7. The method of claim 1, wherein the *Pseudomonas* exotoxin translocation domain comprises an amino acid sequence as set forth in SEQ ID NO:1 and the Pseudomonas exotoxin ADP-ribosylation domain comprises an amino acid sequence as set forth in SEQ ID NO:2.

8. A pharmaceutical composition for the ablation of NK1 receptor expressing cells comprising a cell toxin and a pharmaceutically acceptable excipient, wherein the cell toxin is a substance P-*Pseudomonas* exotoxin disulfide linked conjugate made by a process comprising the following steps:
reacting a polypeptide comprising a *Pseudomonas* exotoxin translocation domain linked to a *Pseudomonas* exotoxin ADP-ribosylation domain, wherein the *Pseudomonas* exotoxin translocation domain comprises at least one reactive sulfhydryl group, with a substance P peptide comprising one additional cysteine residue at its amino terminal end, wherein the cysteine sulfhydryl group is disulfide linked to a di-thiobis (2-nitro)-benzoic acid group, such that after the reaction a disulfide bond is formed between the exotoxin polypeptide and the substance P and a thionitrobenzoate group is released, and
purifying the substance P-*Pseudomonas* exotoxin disulfide linked conjugate from the released thionitrobenzoate group such that the purified conjugate is substantially free of thionitrobenzoate groups.

9. The pharmaceutical composition of claim 8, wherein the *Pseudomonas* exotoxin translocation domain sulfhydryl group located within ten amino acid residues of the translocation domain amino terminus.

10. The pharmaceutical composition of claim 8, wherein the *Pseudomonas* exotoxin translocation domain sulfhydryl group located at the translocation domain amino terminus.

11. The pharmaceutical composition of claim 8, wherein the *Pseudomonas* exotoxin translocation domain sulfhydryl group is a cysteine residue.

12. The pharmaceutical composition of claim 8, wherein the *Pseudomonas* exotoxin translocation domain is covalently linked to the *Pseudomonas* exotoxin ADP-ribosylation domain.

13. The pharamceutical composition of claim 12, wherein the covalent linkage between the *Pseudomonas* exotoxin translocation domain and the *Pseudomonas* exotoxin ADP-ribosylation domain is a peptide bond.

14. The pharmaceutical composition of claim 8, wherein the *Pseudomonas* exotoxin translocation domain comprises an amino acid sequence as set forth in SEQ ID NO:1 and the *Pseudomonas* exotoxin ADP-ribosylation domain comprises an amino acid sequence as set forth in SEQ ID NO:2.

15. The pharmaceutical composition of claim 8, wherein the cell toxin and pharamceutically acceptable excipient are suitable for administration intrathecally, subdurally or directly into the brain parenchyma.

16. A method for ablating an NK1 receptor expressing cell in a patient comprising administering to said patient a cell toxin in a pharmaceutically acceptable excipient in an amount sufficient to ablate an NK1 receptor expressing cell, wherein the cell toxin is a substance P-*Pseudomonas* exotoxin disulfide linked conjugate made by a process comprising the following steps:

reacting a polypeptide comprising a *Pseudomonas* exotoxin translocation domain linked to a *Pseudomonas* exotoxin ADP-ribosylation domain, wherein the *Pseudomonas* exotoxin translocation domain comprises at least one reactive sulfhydryl group, with a substance P peptide comprising one additional cysteine residue at its amino terminal end, wherein the cysteine sulfhydryl group is disulfide linked to a di-thiobis (2-nitro)-benzoic acid group, such that after the reaction a disulfide bond is formed between the exotoxin polypeptide and the substance P and a thionitrobenzoate group is released, and purifying the substance P-*Pseudomonas* exotoxin disulfide linked conjugate from the released thionitrobenzoate group such that the purified conjugate is substantially free of thionitrobenzoate groups.

17. The method of claim 16, wherein the ablated NK1 receptor expressing cell is a dorsal horn cell, a stratum cell or a brain parenchyma cell.

18. A method of treating chronic pain without significantly afftecting basal nociceptive responses comprising administering to a subject in need thereof a cell toxin in a pharmaceutically acceptable excipient in an amount sufficient to treat chronic pain without significantly afftecting basal nociceptive responses, wherein the cell toxin is a substance P-*Pseudomonas* exotoxin disulfide linked conjugate made by a process comprising the following steps:

reacting a polypeptide comprising a *Pseudomonas* exotoxin translocation domain linked to a *Pseudomonas* exotoxin ADP-ribosylation domain, wherein the *Pseudomonas* exotoxin translocation domain comprises at least one reactive sulfhydryl group, with a substance P peptide comprising one additional cysteine residue at its amino terminal end, wherein the cysteine sulfhydryl group is disulfide linked to a di-thiobis (2-nitro)-benzoic acid group, such that after the reaction a disulfide bond is formed between the exotoxin polypeptide and the substance P and a thionitrobenzoate group is released, and purifying the substance P-*Pseudomonas* exotoxin disulfide linked conjugate from the released thionitrobenzoate group such that the purified conjugate is substantially free of thionitrobenzoate groups.

19. The method of claim 18, wherein cell toxin is administered to epineurium cells, perineurium cells, nerve ganglia, nerve sheathers, nerve linings, meninges, pia mater cells, arachnoid membrane cells, dura membrane cells, cells lining a joint or brain or spinal cord parenchymal cells.

* * * * *